US005965390A

United States Patent [19]
Björck et al.

[11] Patent Number: 5,965,390
[45] Date of Patent: Oct. 12, 1999

[54] PROTEIN L AND HYBRID PROTEINS THEREOF

[75] Inventors: Lars Björck, Södra Sandby; Ulf Sjöbring, Lund, both of Sweden

[73] Assignee: Actinova Ltd., Lund, Sweden

[21] Appl. No.: 08/795,475

[22] Filed: Feb. 11, 1997

Related U.S. Application Data

[62] Division of application No. 08/325,278, Oct. 26, 1994, filed as application No. PCT/SE93/00375, Apr. 28, 1993.

[30] Foreign Application Priority Data

Apr. 28, 1992 [SE] Sweden ................................. 9201331

[51] Int. Cl.$^6$ ........................... C12P 21/02; C07H 21/04; C12N 1/21; C12N 15/63
[52] U.S. Cl. ................ 435/69.1; 435/252.3; 435/254.11; 435/320.1; 536/23.1
[58] Field of Search .................................. 536/23.1, 24.1; 435/320.1, 69.1, 257.3, 252.31, 252.33, 254.11, 254.2, 254.21

[56] References Cited

U.S. PATENT DOCUMENTS

| 4,876,194 | 10/1989 | Björck et al. | 435/68.1 |
|---|---|---|---|
| 5,312,901 | 5/1994 | Fahnestock | 530/350 |

FOREIGN PATENT DOCUMENTS

| A2 0255497 | 2/1988 | European Pat. Off. . |
|---|---|---|
| WO 87/05631 | 9/1987 | WIPO . |
| WO 91/19740 | 12/1991 | WIPO . |

OTHER PUBLICATIONS

Kastern et al., "Structure of Peptostreptococcal Protein L and Identification of a Repeated Immunoglobulin Light Chain–binding Domain," *Journal of Biological Chmistry* 267(18):12820–12825, 1992.
Kastern et al., "Protein L, a Bacterial Immunoglobulin–Binding Protein and Possible Virulence Determinant," *Infection and Immunity* 58(5):1217–1222, 1990.
Björck, Lars, "Protein L, A Novel Bacterial Cell Wall Proetin with Affinity for Ig L Chains," *Journal of Immunology* 140(4):0000–0000, 1988.
Björck and Kronvall, "Purification and Some Properties of Streptococcal Protein G, a Novel IgG–Binding Reagent," *Journal of Immunology* 133(2), 969–974, 1984.
Sjöbring et al., "Streptococcal Protein G Gene Structure and Protein Binding Properties," *Journal of Biological Chemistry* 266(1):399–405, 1991.
Forsgren and Sjöquist, "Protein A" From *S. Aureus*: I. Pseudo–Immune Reaction with Humany–Globulin, *Journal of Immunology* 97(6):822–827, 1966.

Akerstrom and Björck, "Protein L: An Immunoglobulin Light Chain–binding Bacterial Protein," *The Journal of Biological Chemistry* 264(33):19740–19746, 1989.
Alberts, *Molecular Biology of The Cell*,$2^{nd}$ ed., Garland Publishing, Inc., New York, 1989, p. 265.
Bowie et al., "Deciphering the Message in Protein Sequences: Tolerance to Amino Acid Substitutions," *Science* 247:1306–1309, 1990.
Burgess et al., "Possible Dissociation of the Heparin–binding and Mitogenic Activities of Heparin–binding (Acidic Fibroblast) Growth Factor–1 from Its Receptor–binding Activities by the Site–directed Mutagenesis of a Single Lysine Residue," *The Journal of Cell Biology* 111:2129–2138, 1990.
Château et al., "On the Interaction between Protein L and Immunoglobulins of Various Mammalian Species," *Scand. J. Immunol.* 37:399–405, 1993.
Elbashir et al., "Antibody response in immunized rabbits measured with bacterial immunoglobulin–binding proteins," *Journal of Immunological Methods* 135:171–179, 1990.
Kihlberg et al., "Protein LG: A Hybrid Molecule with Unique Immunoglobulin Binding Properties," *The Journal of Biological Chemistry* 267(35):25583–25588, 1992.
Lämmler et al., "Characterization of albumin–binding properties of *Peptostreptococcus magnus*," *Can. J. Microbiol.* 35:614–618, 1989.
Lazar et al., "Transforming Growth Factorα: Mutation of Asparic Acid 47 and Leucine 48 Results in Different Biological Activities," *Molecular and Cellular Biology* 8(3):1247–1252, 1988.
Ng and Dillon, "Molecular fingerprinting of isolates and the genus Peptostreptococcus using rRNA genes from *Escherichia coli* and *P. anaerobius*," *Journal of General Microbiology* 137:1323–1331, 1991.
Nilson et al., "Protein L from *Peptostreptococcus magnus* Binds to theκLight Chain Variable Domain," *The Journal of Biological Chemistry* 267(4):2234–2239, 1992.
Patella et al., "A Bacterial Ig–Binding Protein That Activates Human Basophils and Mast Cells," *The Journal of Immunology* 145(9):3054–3061, 1990.

*Primary Examiner*—Nancy Degen
*Attorney, Agent, or Firm*—Seed and Berry LLP

[57] ABSTRACT

The invention relates to sequences of protein L which bind to light chains of immunoglobulins. The invention also relates to hybrid proteins thereof which are able to bind to both light and heavy chains of immunoglobulin G, in particular protein LG. The invention also relates to DNA-sequences which code for the proteins, vectors which include such DNA-sequences, host cells which have been transformed with the vectors, methods for producing the proteins, reagent appliances for separation and identification of immunoglobulins, compositions and pharmaceutical compositions and pharmaceutical compositions which contain the proteins.

11 Claims, 17 Drawing Sheets

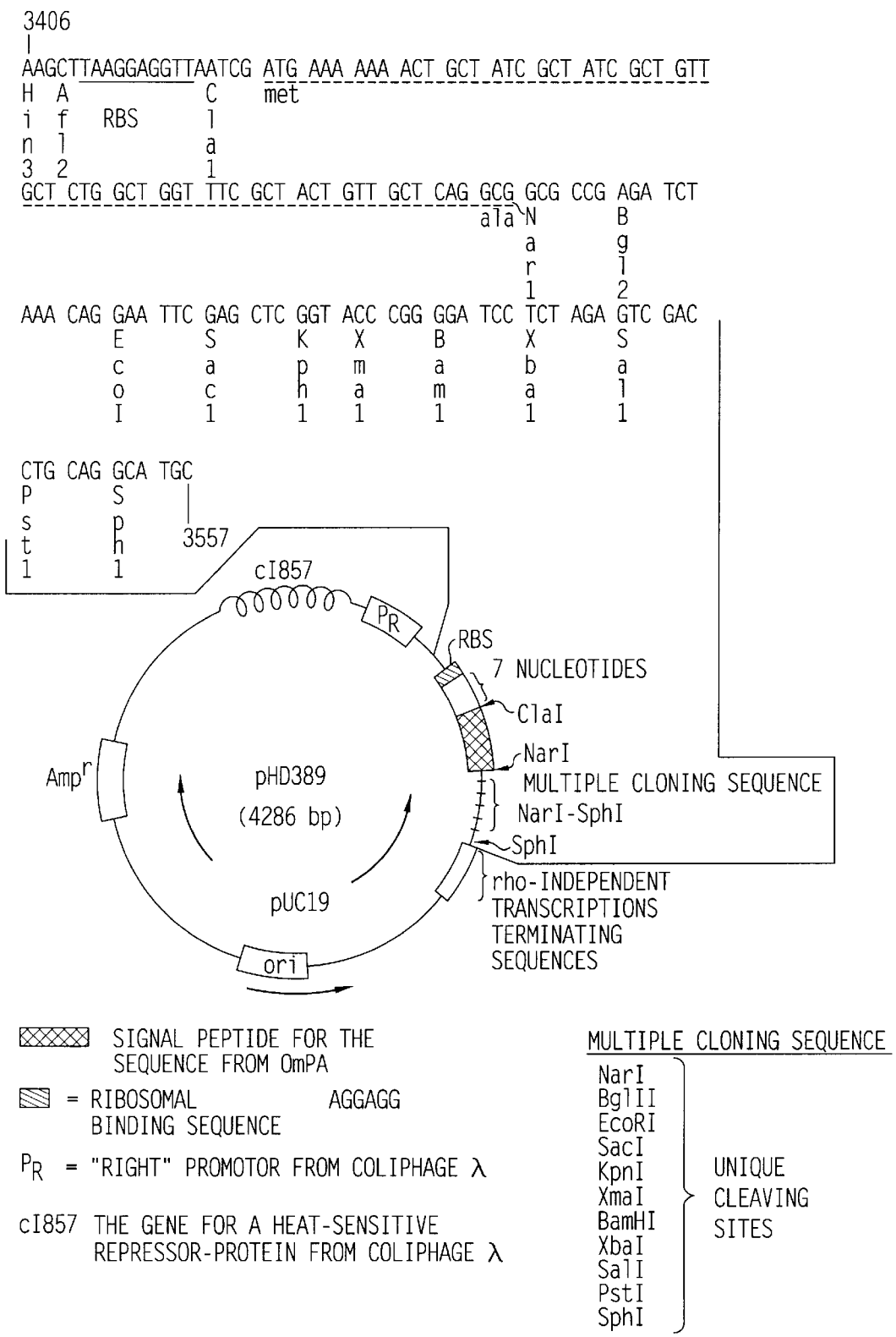
Fig. 1 PLASMA pHD 389. THE RIBOSOMAL BINDING-SEQUENCE (EMPHASIZED WITH A FULL LINE), THE SEQUENCE FOR SIGNAL PEPTIDE FROM ompA (FROM E.coli) (DOTTED LINE) AND RECOGNITION SEQUENCE FOR SEVERAL RESTRICTION ENZYMES ARE SHOWN.

```
                    ┌─── B1
GCG │GTA GAA AAT│AAA GAA GAA ACA CCA GAA ACA CCA GAA ACT GAT TCA GAA GAA GAA GTA    60
Ala │Val Glu Asn│Lys Glu Glu Thr Pro Glu Thr Pro Glu Thr Asp Ser Glu Glu Glu Val
1              5                   10                  15                  20

ACA ATC AAA GCT AAC CTA ATC TTT GCA AAT GGA AGC ACA CAA ACT GCA GAA TTC AAA GGA   120
Thr Ile Lys Ala Asn Leu Ile Phe Ala Asn Gly Ser Thr Gln Thr Ala Glu Phe Lys Gly
                25                  30                  35                  40

ACA TTT GAA AAA GCA ACA TCA GAA GCT TAT GCG TAT GCA GAT ACT TTG AAG AAA GAC AAT   180
Thr Phe Glu Lys Ala Thr Ser Glu Ala Tyr Ala Tyr Ala Asp Thr Leu Lys Lys Asp Asn
                45                  50                  55                  60

GGA GAA TAT ACT GTA GAT GTT GCA GAT AAA GGT TAT ACT TTA AAT ATT AAA TTT GCT GGA   240
Gly Glu Tyr Thr Val Asp Val Ala Asp Lys Gly Tyr Thr Leu Asn Ile Lys Phe Ala Gly
                65                  70                  75                  80

┌── B2
│AAA GAA AAA ACA CCA GAA GAA CCA AAA GAA GAA GTT ACT ATT AAA GCA AAC TTA ATC TAT  300
│Lys Glu Lys Thr Pro Glu Glu Pro Lys Glu Glu Val Thr Ile Lys Ala Asn Leu Ile Tyr
                85                  90                  95                  100

GCA GAT GGA AAA ACA CAA ACA GCA GAA TTC AAA GGA ACA TTT GAA GAA GCA ACA GCA GAA   360
Ala Asp Gly Lys Thr Gln Thr Ala Glu Phe Lys Gly Thr Phe Glu Glu Ala Thr Ala Glu
                105                 110                 115                 120

GCA TAC AGA TAT GCA GAT GCA TTA AAG AAG GAC AAT GGA GAA TAT ACA GTA GAC GTT GCA   420
Ala Tyr Arg Tyr Ala Asp Ala Leu Lys Lys Asp Asn Gly Glu Tyr Thr Val Asp Val Ala
                125                 130                 135                 140
                                                 ┌── B3
GAT AAA GGT TAT ACT TTA AAT ATT AAA TTT GCT GGA│AAA GAA AAA ACA CCA GAA GAA CCA   480
Asp Lys Gly Tyr Thr Leu Asn Ile Lys Phe Ala Gly│Lys Glu Lys Thr Pro Glu Glu Pro
                145                 150                 155                 160
```

*Fig. 2A*

```
AAA GAA GAA GTT ACT ATT AAA GCA AAC TTA ATC TAT GCA GAT GGA AAA ACA CAA ACA GCA    540
Lys Glu Glu Val Thr Ile Lys Ala Asn Leu Ile Tyr Ala Asp Gly Lys Thr Gln Thr Ala
            165                 170                 175                 180

GAA TTC AAA GGA ACA TTT GAA GAA GCA ACA GCA GAA GCA TAC AGA TAT GCT GAC TTA TTA    600
Glu Phe Lys Gly Thr Phe Glu Glu Ala Thr Ala Glu Ala Tyr Arg Tyr Ala Asp Leu Leu
            185                 190                 195                 200

GCA AAA GAA AAT GGT AAA TAT ACA GTA GAC GTT GCA GAT AAA GGT TAT ACT TTA AAT ATT    660
Ala Lys Glu Asn Gly Lys Tyr Thr Val Asp Val Ala Asp Lys Gly Tyr Thr Leu Asn Ile
            205                 210                 215                 220

┌── B4
AAA TTT GCT GGA│AAA GAA AAA ACA CCA GAA GAA CCA AAA GAA GAA GTT ACT ATT AAA GCA    720
Lys Phe Ala Gly│Lys Glu Lys Thr Pro Glu Glu Pro Lys Glu Glu Val Thr Ile Lys Ala
               225                 230                 235                 240

AAC TTA ATC TAT GCA GAT GGA AAA ACT CAA ACA GCA GAG TTC AAA GGA ACA TTT GCA GAA    780
Asn Leu Ile Tyr Ala Asp Gly Lys Thr Gln Thr Ala Glu Phe Lys Gly Thr Phe Ala Glu
            245                 250                 255                 260

GCA ACA GCA GAA GCA TAC AGA TAC GCT GAC TTA TTA GCA AAA GAA AAT GGT AAA TAT ACA    840
Ala Thr Ala Glu Ala Tyr Arg Tyr Ala Asp Leu Leu Ala Lys Glu Asn Gly Lys Tyr Thr
            265                 270                 275                 280

┌── B5
GCA GAC TTA GAA GAT GGT GGA TAC ACT ATT AAT ATT AGA TTT GCA GGT│AAG AAA GTT GAC    900
Ala Asp Leu Glu Asp Gly Gly Tyr Thr Ile Asn Ile Arg Phe Ala Gly│Lys Lys Val Asp
            285                 290                 295                 300
                                                                ←─────────

┐    ┌── C1
GAA AAA CCA GAA GAA│CCC ATG│GAC│ACT TAC AAA TTA ATC CTT AAT GGT AAA ACA TTG AAA    960
Glu Lys Pro Glu Glu│Pro Met│Asp│Thr Tyr Lys Leu Ile Leu Asn Gly Lys Thr Leu Lys
            305         310         315                 320
─────────────                              ─────────────────────→
```

*Fig. 2B*

```
GGC GAA ACA ACT ACT GAA GCT GTT GAT GCT GCT ACT GCA GAA AAA GTC TTC AAA CAA TAC   1020
Gly Glu Thr Thr Thr Glu Ala Val Asp Ala Ala Thr Ala Glu Lys Val Phe Lys Gln Tyr
                325                 330                 335                 340

GCT AAC GAC AAC GGT GTT GAC GGT GAA TGG ACT TAC GAC GAT GCG ACT AAG ACC TTT ACA   1080
Ala Asn Asp Asn Gly Val Asp Gly Glu Trp Thr Tyr Asp Asp Ala Thr Lys Thr Phe Thr
                345                 350                 355                 360

┌─── D                                              ┌─── C2
GTT ACT GAA│AAA CCA GAA GTG ATC GAT GCG TCT GAA TTA ACA CCA GCC GTG ACA│ACT TAC   1140
Val Thr Glu│Lys Pro Glu Val Ile Asp Ala Ser Glu Leu Thr Pro Ala Val Thr│Thr Tyr
                365                 370                 375                 380

AAA CTT GTT ATT AAT GGT AAA ACA TTG AAA GGC GAA ACA ACT ACT AAA GCA GTA GAC GCA   1200
Lys Leu Val Ile Asn Gly Lys Thr Leu Lys Gly Glu Thr Thr Thr Lys Ala Val Asp Ala
                385                 390                 395                 400

GAA ACT GCA GAA AAA GCC TTC AAA CAA TAC GCT AAC GAC AAC GGT GTT GAT GGT GTT TGG   1260
Glu Thr Ala Glu Lys Ala Phe Lys Gln Tyr Ala Asn Asp Asn Gly Val Asp Gly Val Trp
                405                 410                 415                 420

┌─
ACT TAT GAT GAT GCG ACT AAG ACC TTT ACG GTA ACT GAA│ATG TAA TAA                    1308
Thr Tyr Asp Asp Ala Thr Lys Thr Phe Thr Val Thr Glu│Met  -   -
                425                 430
                                    ◄───────────────
```

*Fig. 2C*

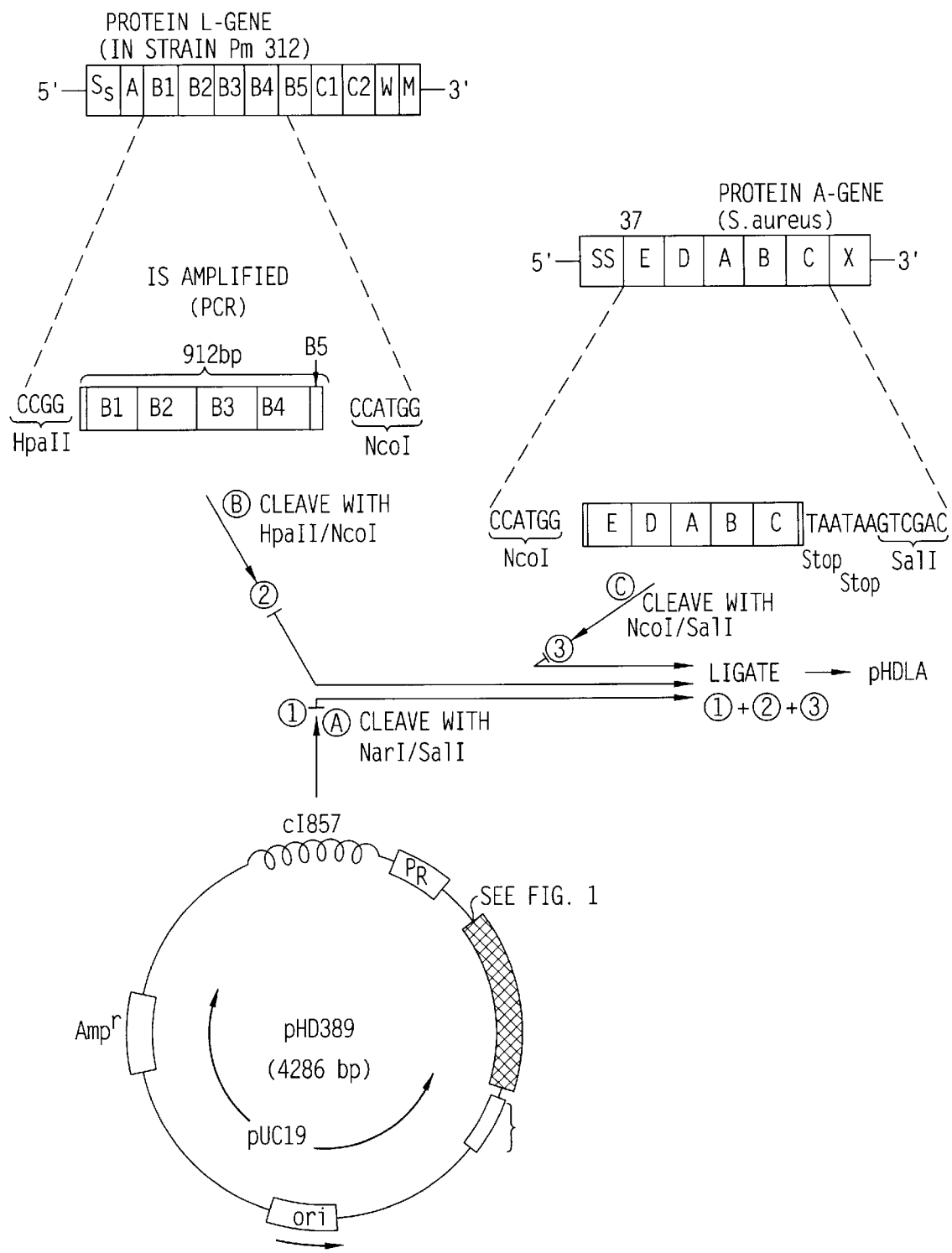
Fig. 5A  SCHEMATIC OVERALL VIEW OF THE PRODUCTION OF PROTEIN LA

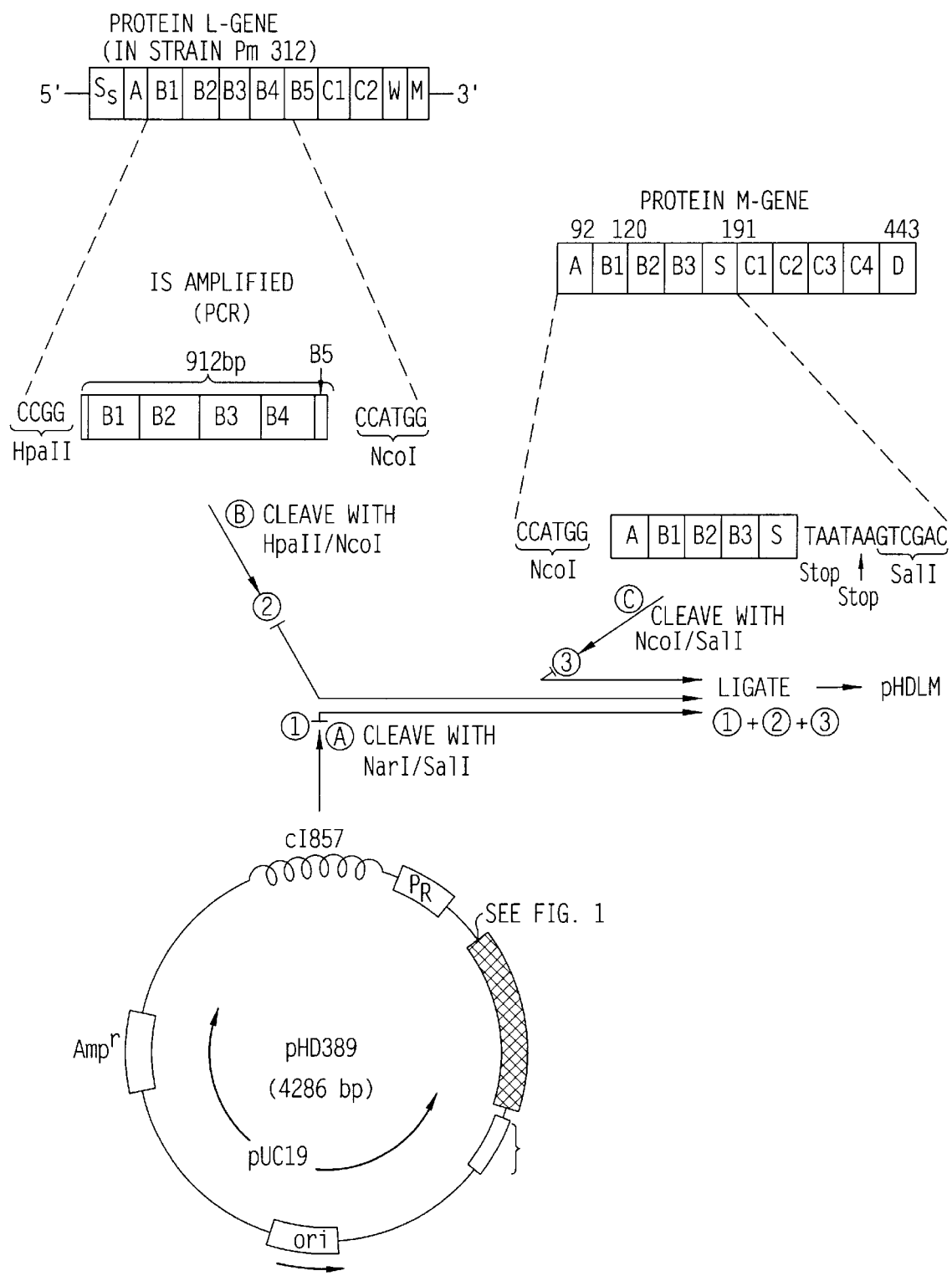
Fig. 5B  SCHEMATIC OVERALL VIEW OF THE PRODUCTION OF PROTEIN LM

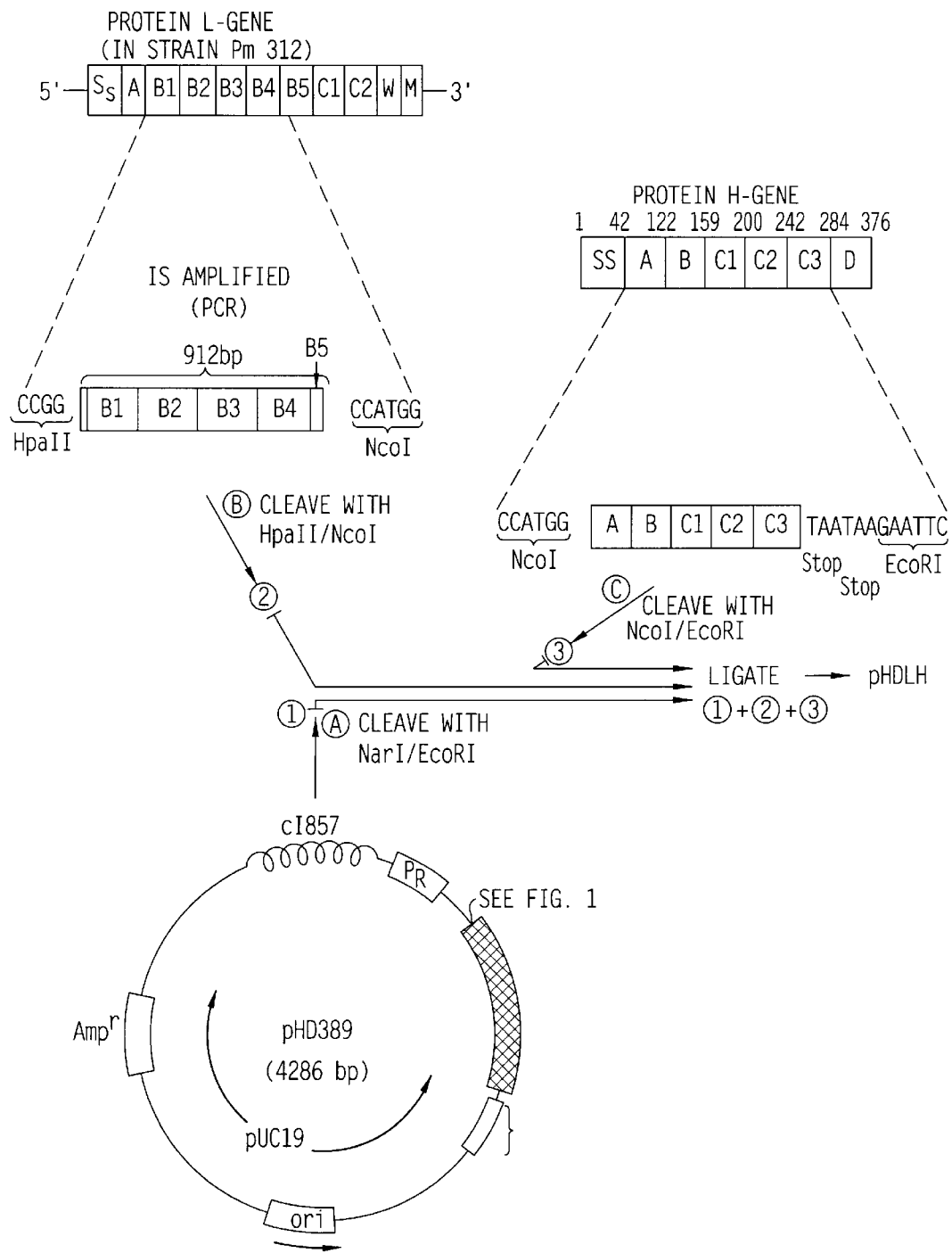
Fig. 5C  SCHEMATIC OVERALL VIEW OF THE PRODUCTION OF PROTEIN LH

```
AAC GGT GAT GGT AAT CCT AGG GAA GTT ATA GAA GAT CTT GCA GCA AAC      48
Asn Gly Asp Gly Asn Pro Arg Glu Val Ile Glu Asp Leu Ala Ala Asn
 1           5                  10                  15

AAT CCC GCA ATA CAA AAT ATA CGT TTA CGT CAC GAA AAC AAG GAC TTA      96
Asn Pro Ala Ile Gln Asn Ile Arg Leu Arg His Glu Asn Lys Asp Leu
             20                  25                  30

AAA GCG AGA TTA GAG AAT GCA ATG GAA GTT GCA GGA AGA GAT TTT AAG     144
Lys Ala Arg Leu Glu Asn Ala Met Glu Val Ala Gly Arg Asp Phe Lys
         35                  40                  45

AGA GCT GAA GAA CTT GAA AAA GCA AAA CAA GCC TTA GAA GAC CAG CGT     192
Arg Ala Glu Glu Leu Glu Lys Ala Lys Gln Ala Leu Glu Asp Gln Arg
     50                  55                  60

AAA GAT TTA GAA ACT AAA TTA AAA GAA CTA CAA CAA GAC TAT GAC TTA     240
Lys Asp Leu Glu Thr Lys Leu Lys Glu Leu Gln Gln Asp Tyr Asp Leu
 65                  70                  75                  80

GCA AAG GAA TCA ACA AGT TGG GAT AGA CAA AGA CTT GAA AAA GAG TTA     288
Ala Lys Glu Ser Thr Ser Trp Asp Arg Gln Arg Leu Glu Lys Glu Leu
                 85                  90                  95

GAA GAG AAA AAG GAA GCT CTT GAA TTA GCG ATA GAC CAG GCA AGT CGG     336
Glu Glu Lys Lys Glu Ala Leu Glu Leu Ala Ile Asp Gln Ala Ser Arg
             100                 105                 110

GAC TAC CAT AGA GCT ACC GCT TTA GAA AAA GAG TTA GAA GAG AAA AAG     384
Asp Tyr His Arg Ala Thr Ala Leu Glu Lys Glu Leu Glu Glu Lys Lys
         115                 120                 125

AAA GCT CTT GAA TTA GCG ATA GAC CAA GCG AGT CAG GAC TAT AAT AGA     432
Lys Ala Leu Glu Leu Ala Ile Asp Gln Ala Ser Gln Asp Tyr Asn Arg
     130                 135                 140

GCT AAC GTC TTA GAA AAA GAG TTA GAA ACG ATT ACT AGA GAA CAA GAG     480
Ala Asn Val Leu Glu Lys Glu Leu Glu Thr Ile Thr Arg Glu Gln Glu
145                 150                 155                 160

ATT AAT CGT AAT CTT TTA GGC AAT GCA AAA CTT GAA CTT GAT CAA CTT     528
Ile Asn Arg Asn Leu Leu Gly Asn Ala Lys Leu Glu Leu Asp Gln Leu
                 165                 170                 175
```

*Fig. 7A*

```
TCA TCT GAA AAA GAG CAG CTA ACG ATC GAA AAA GCA AAA CTT GAG GAA    576
Ser Ser Glu Lys Glu Gln Leu Thr Ile Glu Lys Ala Lys Leu Glu Glu
            180                 185                 190

GAA AAA CAA ATC TCA GAC GCA AGT CGT CAA AGC CTT CGT CGT GAC TTG    624
Glu Lys Gln Ile Ser Asp Ala Ser Arg Gln Ser Leu Arg Arg Asp Leu
            195                 200                 205

GAC GCA TCA CGT GAA GCT AAG AAA CAG GTT GAA AAA GAT TTA GCA AAC    672
Asp Ala Ser Arg Glu Ala Lys Lys Gln Val Glu Lys Asp Leu Ala Asn
            210                 215                 220

TTG ACT GCT GAA CTT GAT AAG GTT AAA GAA GAC AAA CAA ATC TCA GAC    720
Leu Thr Ala Glu Leu Asp Lys Val Lys Glu Asp Lys Gln Ile Ser Asp
225                 230                 235                 240

GCA AGC CGT CAA CGG CTT CGC CGT GAC TTG GAC GCA TCA CGT GAA GCT    768
Ala Ser Arg Gln Arg Leu Arg Arg Asp Leu Asp Ala Ser Arg Glu Ala
                245                 250                 255

AAG AAA CAG GTT GAA AAA GAT TTA GCA AAC TTG ACT GCT GAA CTT GAT    816
Lys Lys Gln Val Glu Lys Asp Leu Ala Asn Leu Thr Ala Glu Leu Asp
                260                 265                 270

AAG GTT AAA GAA GAA AAA CAA ATC TCA GAC GCA AGC CGT CAA CGG CTT    864
Lys Val Lys Glu Glu Lys Gln Ile Ser Asp Ala Ser Arg Gln Arg Leu
            275                 280                 285

CGC CGT GAC TTG GAC GCA TCA CGT GAA GCT AAG AAA CAA GTT GAA AAA    912
Arg Arg Asp Leu Asp Ala Ser Arg Glu Ala Lys Lys Gln Val Glu Lys
            290                 295                 300

GCT TTA GAA GAA GCA AAC AGC AAA TTA GCT GCT CTT GAA AAA CTT AAC    960
Ala Leu Glu Glu Ala Asn Ser Lys Leu Ala Ala Leu Glu Lys Leu Asn
305                 310                 315                 320

AAA GAG CTT GAA GAA AGC AAG AAA TTA ACA GAA AAA GAA AAA GCT GAA   1008
Lys Glu Leu Glu Glu Ser Lys Lys Leu Thr Glu Lys Glu Lys Ala Glu
                325                 330                 335

CTA CAA GCA AAA CTT GAA GCA GAA GCA AAA GCA CTC AAA GAA CAA TTA   1056
Leu Gln Ala Lys Leu Glu Ala Glu Ala Lys Ala Leu Lys Glu Gln Leu
            340                 345                 350
```

*Fig. 7B* AMINO ACID SEQUENCE AND NUCLEIC ACID SEQUENCE FOR PROTEIN M1, IgG-BINDING SOMEWHERE BETWEEN AMINO ACID 1-190.

```
GCG AAA CAA GCT GAA GAA CTC GCA AAA CTA AGA GCT GGA AAA GCA TCA       1104
Ala Lys Gln Ala Glu Glu Leu Ala Lys Leu Arg Ala Gly Lys Ala Ser
        355                 360                 365

GAC TCA CAA ACC CCT GAT ACA AAA CCA GGA AAC AAA GCT CTT CCA GGT       1152
Asp Ser Gln Thr Pro Asp Thr Lys Pro Gly Asn Lys Val Leu Pro Gly
        370                 375                 380

AAA GGT CAA GCA CCA CAA GCA GGT ACA AAA CCT AAC CAA AAC AAA GCA       1200
Lys Gly Gln Ala Pro Gln Ala Gly Thr Lys Pro Asn Gln Asn Lys Ala
385                 390                 395                 400

CCA ATG AAG GAA ACT AAG AGA CAG TTA CCA TCA ACA GGT GAA ACA GCT       1248
Pro Met Lys Glu Thr Lys Arg Gln Leu Pro Ser Thr Gly Glu Thr Ala
                405                 410                 415

AAC CCA TTC TTC ACA GCG GCA CGC GTT ACT GTT ATG GCA ACA GCT GGA       1296
Asn Pro Phe Phe Thr Ala Ala Arg Val Thr Val Met Ala Thr Ala Gly
            420                 425                 430

GTA GCA GCA GTT GTA AAA CGC AAA GAA GAA AAC TAA                       1329
Val Ala Ala Val Val Lys Arg Lys Glu Glu Asn >>>
            435                 440
```

*Fig. 7C*

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
       (A) LENGTH: 305 amino acids
       (B) TYPE: amino acid
       (C) STRANDEDNESS: unknown
       (D) TOPOLOGY: unknown (ii) MOLECULE TYPE: protein (iii) HYPOTHETICAL: NO (vi) ORIGINAL SOURCE:
       (A) ORGANISM: Escherichia coli LE392/pHDL, DSM 7054

(xi) SEQUENCE DESCRIPTION: SEQ ID NO:1:

```
Ala Val Glu Asn Lys Glu Glu Thr Pro Glu Thr Pro Glu Thr Asp Ser
1               5                  10                  15

Glu Glu Glu Val Thr Ile Lys Ala Asn Leu Ile Phe Ala Asn Gly Ser
            20                  25                  30

Thr Gln Thr Ala Glu Phe Lys Gly Thr Phe Glu Lys Ala Thr Ser Glu
        35                  40                  45

Ala Tyr Ala Tyr Ala Asp Thr Leu Lys Lys Asp Asn Gly Glu Tyr Thr
    50                  55                  60

Val Asp Val Ala Asp Lys Gly Tyr Thr Leu Asn Ile Lys Phe Ala Gly
65                  70                  75                  80

Lys Glu Lys Thr Pro Glu Glu Pro Lys Glu Val Thr Ile Lys Ala
                85                  90                  95

Asn Leu Ile Tyr Ala Asp Gly Lys Thr Gln Thr Ala Glu Phe Lys Gly
                100                 105                 110

Thr Phe Glu Glu Ala Thr Ala Glu Ala Tyr Arg Tyr Ala Asp Ala Leu
            115                 120                 125

Lys Lys Asp Asn Gly Glu Tyr Thr Val Asp Val Ala Asp Lys Gly Tyr
    130                 135                 140

Thr Leu Asn Ile Lys Phe Ala Gly Lys Glu Lys Thr Pro Glu Glu Pro
145                 150                 155                 160

Lys Glu Glu Val Thr Ile Lys Ala Asn Leu Ile Tyr Ala Asp Gly Lys
                165                 170                 175

Thr Gln Thr Ala Glu Phe Lys Gly Thr Phe Glu Glu Ala Thr Ala Glu
            180                 185                 190

Ala Tyr Arg Tyr Ala Asp Leu Leu Ala Lys Glu Asn Gly Lys Tyr Thr
    195                 200                 205

Val Asp Val Ala Asp Lys Gly Tyr Thr Leu Asn Ile Lys Phe Ala Gly
    210                 215                 220

Lys Glu Lys Thr Pro Glu Glu Pro Lys Glu Val Thr Ile Lys Ala
225                 230                 235                 240

Asn Leu Ile Tyr Ala Asp Gly Lys Thr Gln Thr Ala Glu Phe Lys Gly
                245                 250                 255

Thr Phe Ala Glu Ala Thr Ala Glu Ala Tyr Arg Tyr Ala Asp Leu Leu
            260                 265                 270

Ala Lys Glu Asn Gly Lys Tyr Thr Ala Asp Leu Glu Asp Gly Gly Tyr
    275                 280                 285

Thr Ile Asn Ile Arg Phe Ala Gly Lys Lys Val Asp Glu Lys Pro Glu
```

```
            290                 295                 300
Glu
305

(2) INFORMATION FOR SEQ ID NO:2:

(i) SEQUENCE CHARACTERISTICS:
         (A) LENGTH: 921 base pairs
         (B) TYPE: nucleic acid
         (C) STRANDEDNESS: double
         (D) TOPOLOGY: unknown (ii) MOLECULE TYPE: DNA (genomic)

(iii) HYPOTHETICAL: NO (vi) ORIGINAL SOURCE:
         (A) ORGANISM: Escherichia coli LE392/pHDL, DSM 7054

(xi) SEQUENCE DESCRIPTION: SEQ ID NO:2:

GCGGTAGAAA ATAAAGAAGA ACACCAGAAA ACACCAGAAA CTGATTCAGA AGAAGAAGTA    60

ACAATCAAAG CTAACCTAAT CTTTGCAAAT GGAAGCACAC AAACTGCAGA ATTCAAAGGA   120

ACATTTGAAA AAGCAACATC AGAAGCTTAT GCGTATGCAG ATACTTTGAA GAAAGACAAT   180

GGAGAATATA CTGTAGATGT TGCAGATAAA GGTTATACTT TAAATATTAA ATTTGCTGGA   240

AAAGAAAAAA CACCAGAAGA ACCAAAAGAA GAAGTTACTA TTAAAGCAAA CTTAATCTAT   300

GCAGATGGAA AAACACAAAC AGCAGAATTC AAAGGAACAT TTGAAGAAGC AACAGCAGAA   360

GCATACAGAT ATGCAGATGC ATTAAAGAAG GACAATGGAG AATATACAGT AGACGTTGCA   420

GATAAAGGTT ATACTTTAAA TATTAAATTT GCTGGAAAAG AAAAAACACC AGAAGAACCA   480

AAAGAAGAAG TTACTATTAA AGCAAACTTA ATCTATGCAG ATGGAAAAAC ACAAACAGCA   540

GAATTCAAAG GAACATTTGA AGAAGCAACA GCAGAAGCAT ACAGATATGC TGACTTATTA   600

GCAAAAGAAA ATGGTAAATA TACAGTAGAC GTTGCAGATA AAGGTTATAC TTTAAATATT   660

AAATTTGCTG GAAAAGAAAA AACACCAGAA GAACCAAAAG AAGAAGTTAC TATTAAAGCA   720

AACTTAATCT ATGCAGATGG AAAAACTCAA ACAGCAGAGT TCAAAGGAAC ATTTGCAGAA   780

GCAACAGCAG AAGCATACAG ATACGCTGAC TTATTAGCAA AAGAAAATGG TAAATATACA   840

GCAGACTTAG AAGATGGTGG ATACACTATT AATATTGATT TGCAGGTAA GAAAGTTGAC   900

GAAAAACCAG AAGAATAATA A                                              921

(2) INFORMATION FOR SEQ ID NO:3:

(i) SEQUENCE CHARACTERISTICS:
         (A) LENGTH: 434 amino acids
         (B) TYPE: amino acid
         (C) STRANDEDNESS: unknown
         (D) TOPOLOGY: unknown (ii) MOLECULE TYPE: protein (iii) HYPOTHETICAL: NO (vi) ORIGINAL SOURCE:
         (A) ORGANISM: Escherichia coli LE392/pHDLG, DSM 7055

(xi) SEQUENCE DESCRIPTION: SEQ ID NO:3:

Ala Val Glu Asn Lys Glu Glu Thr Pro Glu Thr Pro Glu Thr Asp Ser
1               5                  10                  15

Glu Glu Glu Val Thr Ile Lys Ala Asn Leu Ile Phe Ala Asn Gly Ser
            20                  25                  30

Thr Gln Thr Ala Glu Phe Lys Gly Thr Phe Glu Lys Ala Thr Ser Glu
```

-continued

```
                35                  40                  45
Ala Tyr Ala Tyr Ala Asp Thr Leu Lys Lys Asp Asn Gly Glu Tyr Thr
    50                  55                  60
Val Asp Val Ala Asp Lys Gly Tyr Thr Leu Asn Ile Lys Phe Ala Gly
65                  70                  75                  80
Lys Glu Lys Thr Pro Glu Glu Pro Lys Glu Glu Val Thr Ile Lys Ala
                85                  90                  95
Asn Leu Ile Tyr Ala Asp Gly Lys Thr Gln Thr Ala Glu Phe Lys Gly
                100                 105                 110
Thr Phe Glu Glu Ala Thr Ala Glu Ala Tyr Arg Tyr Ala Asp Ala Leu
                115                 120                 125
Lys Lys Asp Asn Gly Glu Tyr Thr Val Asp Val Ala Asp Lys Gly Tyr
                130                 135                 140
Thr Leu Asn Ile Lys Phe Ala Gly Lys Glu Lys Thr Pro Glu Glu Pro
145                 150                 155                 160
Lys Glu Glu Val Thr Ile Lys Ala Asn Leu Ile Tyr Ala Asp Gly Lys
                165                 170                 175
Thr Gln Thr Ala Glu Phe Lys Gly Thr Phe Glu Glu Ala Thr Ala Glu
                180                 185                 190
Ala Tyr Arg Tyr Ala Asp Leu Leu Ala Lys Glu Asn Gly Lys Tyr Thr
                195                 200                 205
Val Asp Val Ala Asp Lys Gly Tyr Thr Leu Asn Ile Lys Phe Ala Gly
                210                 215                 220
Lys Glu Lys Thr Pro Glu Glu Pro Lys Glu Glu Val Thr Ile Lys Ala
225                 230                 235                 240
Asn Leu Ile Tyr Ala Asp Gly Lys Thr Gln Thr Ala Glu Phe Lys Gly
                245                 250                 255
Thr Phe Ala Glu Ala Thr Ala Glu Ala Tyr Arg Tyr Ala Asp Leu Leu
                260                 265                 270
Ala Lys Glu Asn Gly Lys Tyr Thr Ala Asp Leu Glu Asp Gly Gly Tyr
                275                 280                 285
Thr Ile Asn Ile Arg Phe Ala Gly Lys Lys Val Asp Glu Lys Pro Glu
                290                 295                 300
Glu Pro Met Asp Thr Tyr Lys Leu Ile Leu Asn Gly Lys Thr Leu Lys
305                 310                 315                 320
Gly Glu Thr Thr Thr Glu Ala Val Asp Ala Ala Thr Ala Glu Lys Val
                325                 330                 335
Phe Lys Gln Tyr Ala Asn Asp Asn Gly Val Asp Gly Glu Trp Thr Tyr
                340                 345                 350
Asp Asp Ala Thr Lys Thr Phe Thr Val Thr Glu Lys Pro Glu Val Ile
                355                 360                 365
Asp Ala Ser Glu Leu Thr Pro Ala Val Thr Thr Tyr Lys Leu Val Ile
                370                 375                 380
Asn Gly Lys Thr Leu Lys Gly Glu Thr Thr Thr Lys Ala Val Asp Ala
385                 390                 395                 400
Glu Thr Ala Glu Lys Ala Phe Lys Gln Tyr Ala Asn Asp Asn Gly Val
                405                 410                 415
Asp Gly Val Trp Thr Tyr Asp Asp Ala Thr Lys Thr Phe Thr Val Thr
                420                 425                 430
Glu Met
```

(2) INFORMATION FOR SEQ ID NO:4:

(i) SEQUENCE CHARACTERISTICS:

(A) LENGTH: 1308 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (vi) ORIGINAL SOURCE:
        (A) ORGANISM: Escherichia coli L392/pHDLG, DSM 7055

(xi) SEQUENCE DESCRIPTION: SEQ ID NO:4:

```
GCGGTAGAAA ATAAAGAAGA ACACCAGAAA ACACCAGAAA CTGATTCAGA AGAAGAAGTA      60

ACAATCAAAG CTAACCTAAT CTTTGCAAAT GGAAGCACAC AAACTGCAGA ATTCAAAGGA     120

ACATTTGAAA AAGCAACATC AGAAGCTTAT GCGTATGCAG ATACTTTGAA GAAAGACAAT     180

GGAGAATATA CTGTAGATGT TGCAGATAAA GGTTATACTT TAAATATTAA ATTTGCTGGA     240

AAAGAAAAAA CACCAGAAGA ACCAAAAGAA GAAGTTACTA TTAAAGCAAA CTTAATCTAT     300

GCAGATGGAA AAACACAAAC AGCAGAATTC AAAGGAACAT TTGAAGAAGC AACAGCAGAA     360

GCATACAGAT ATGCAGATGC ATTAAAGAAG GACAATGGAG AATATACAGT AGACGTTGCA     420

GATAAAGGTT ATACTTTAAA TATTAAATTT GCTGGAAAAG AAAAAACACC AGAAGAACCA     480

AAAGAAGAAG TTACTATTAA AGCAAACTTA ATCTATGCAG ATGGAAAAAC ACAAACAGCA     540

GAATTCAAAG GAACATTTGA AGAAGCAACA GCAGAAGCAT ACAGATATGC TGACTTATTA     600

GCAAAAGAAA ATGGTAAATA TACAGTAGAC GTTGCAGATA AAGGTTATAC TTTAAATATT     660

AAATTTGCTG GAAAAGAAAA AACACCAGAA GAACCAAAAG AAGAAGTTAC TATTAAAGCA     720

AACTTAATCT ATGCAGATGG AAAAACTCAA ACAGCAGAGT TCAAAGGAAC ATTTGCAGAA     780

GCAACAGCAG AAGCATACAG ATACGCTGAC TTATTAGCAA AAGAAATGG TAAATATACA      840

GCAGACTTAG AAGATGGTGG ATACACTATT AATATTAGAT TTGCAGGTAA GAAAGTTGAC     900

GAAAAACCAG AAGAACCCAT GGACACTTAC AAATTAATCC TTAATGGTAA AACATTGAAA     960

GGCGAAACAA CTACTGAAGC TGTTGATGCT GCTACTGCAG AAAAAGTCTT CAAACAATAC    1020

GCTAACGACA ACGGTGTTGA CGGTGAATGG ACTTACGACG ATGCGACTAA GACCTTTACA    1080

GTTACTGAAA AACCAGAAGT GATCGATGCG TCTGAATTAA CACCAGCCGT GACAACTTAC    1140

AAACTTGTTA TTAATGGTAA AACATTGAAA GGCGAAACAA CTACTAAAGC AGTAGACGCA    1200

GAAACTGCAG AAAAAGCCTT CAAACAATAC GCTAACGACA ACGGTGTTGA TGGTGTTTGG    1260

ACTTATGATG ATGCGACTAA GACCTTTACG GTAACTGAAA TGTAATAA                1308
```

(2) INFORMATION FOR SEQ ID NO:5:

(i) SEQUENCE CHARACTERISTICS:
        (A) LENGTH: 1332 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (ix) FEATURE:
        (A) NAME/KEY: CDS
        (B) LOCATION: 1..1329

(xi) SEQUENCE DESCRIPTION: SEQ ID NO:5:

```
AAC GGT GAT GGT AAT CCT AGG GAA GTT ATA GAA GAT CTT GCA GCA AAC        48
Asn Gly Asp Gly Asn Pro Arg Glu Val Ile Glu Asp Leu Ala Ala Asn
 1               5                  10                  15
```

-continued

| | |
|---|---|
| AAT CCC GCA ATA CAA AAT ATA CGT TTA CGT CAC GAA AAC AAG GAC TTA<br>Asn Pro Ala Ile Gln Asn Ile Arg Leu Arg His Glu Asn Lys Asp Leu<br>                    20                       25                    30 | 96 |
| AAA GCG AGA TTA GAG AAT GCA ATG GAA GTT GCA GGA AGA GAT TTT AAG<br>Lys Ala Arg Leu Glu Asn Ala Met Glu Val Ala Gly Arg Asp Phe Lys<br>       35                      40                       45 | 144 |
| AGA GCT GAA GAA CTT GAA AAA GCA AAA CAA GCC TTA GAA GAC CAG CGT<br>Arg Ala Glu Glu Leu Glu Lys Ala Lys Gln Ala Leu Glu Asp Gln Arg<br>50                      55                      60 | 192 |
| AAA GAT TTA GAA ACT AAA TTA AAA GAA CTA CAA CAA GAC TAT GAC TTA<br>Lys Asp Leu Glu Thr Lys Leu Lys Glu Leu Gln Gln Asp Tyr Asp Leu<br>65                      70                      75                      80 | 240 |
| GCA AAG GAA TCA ACA AGT TGG GAT AGA CAA AGA CTT GAA AAA GAG TTA<br>Ala Lys Glu Ser Thr Ser Trp Asp Arg Gln Arg Leu Glu Lys Glu Leu<br>                      85                       90                      95 | 288 |
| GAA GAG AAA AAG GAA GCT CTT GAA TTA GCG ATA GAC CAG GCA AGT CGG<br>Glu Glu Lys Lys Glu Ala Leu Glu Leu Ala Ile Asp Gln Ala Ser Arg<br>                    100                   105                  110 | 336 |
| GAC TAC CAT AGA GCT ACC GCT TTA GAA AAA GAG TTA GAA GAG AAA AAG<br>Asp Tyr His Arg Ala Thr Ala Leu Glu Lys Glu Leu Glu Glu Lys Lys<br>                 115                   120                  125 | 384 |
| AAA GCT CTT GAA TTA GCG ATA GAC CAA GCG AGT CAG GAC TAT AAT AGA<br>Lys Ala Leu Glu Leu Ala Ile Asp Gln Ala Ser Gln Asp Tyr Asn Arg<br>130                     135                   140 | 432 |
| GCT AAC GTC TTA GAA AAA GAG TTA GAA ACG ATT ACT AGA GAA CAA GAG<br>Ala Asn Val Leu Glu Lys Glu Leu Glu Thr Ile Thr Arg Glu Gln Glu<br>145                   150                   155                  160 | 480 |
| ATT AAT CGT AAT CTT TTA GGC AAT GCA AAA CTT GAA CTT GAT CAA CTT<br>Ile Asn Arg Asn Leu Leu Gly Asn Ala Lys Leu Glu Leu Asp Gln Leu<br>                 165                   170                  175 | 528 |
| TCA TCT GAA AAA GAG CAG CTA ACG ATC GAA AAA GCA AAA CTT GAG GAA<br>Ser Ser Glu Lys Glu Gln Leu Thr Ile Glu Lys Ala Lys Leu Glu Glu<br>                 180                   185                  190 | 576 |
| GAA AAA CAA ATC TCA GAC GCA AGT CGT CAA AGC CTT CGT CGT GAC TTG<br>Glu Lys Gln Ile Ser Asp Ala Ser Arg Gln Ser Leu Arg Arg Asp Leu<br>                 195                   200                  205 | 624 |
| GAC GCA TCA CGT GAA GCT AAG AAA CAG GTT GAA AAA GAT TTA GCA AAC<br>Asp Ala Ser Arg Glu Ala Lys Lys Gln Val Glu Lys Asp Leu Ala Asn<br>210                     215                   220 | 672 |
| TTG ACT GCT GAA CTT GAT AAG GTT AAA GAA GAC AAA CAA ATC TCA GAC<br>Leu Thr Ala Glu Leu Asp Lys Val Lys Glu Asp Lys Gln Ile Ser Asp<br>225                   230                   235                  240 | 720 |
| GCA AGC CGT CAA CGG CTT CGC CGT GAC TTG GAC GCA TCA CGT GAA GCT<br>Ala Ser Arg Gln Arg Leu Arg Arg Asp Leu Asp Ala Ser Arg Glu Ala<br>                 245                   250                  255 | 768 |
| AAG AAA CAG GTT GAA AAA GAT TTA GCA AAC TTG ACT GCT GAA CTT GAT<br>Lys Lys Gln Val Glu Lys Asp Leu Ala Asn Leu Thr Ala Glu Leu Asp<br>                 260                   265                  270 | 816 |
| AAG GTT AAA GAA GAA AAA CAA ATC TCA GAC GCA AGC CGT CAA CGG CTT<br>Lys Val Lys Glu Glu Lys Gln Ile Ser Asp Ala Ser Arg Gln Arg Leu<br>                 275                   280                  285 | 864 |
| CGC CGT GAC TTG GAC GCA TCA CGT GAA GCT AAG AAA CAA GTT GAA AAA<br>Arg Arg Asp Leu Asp Ala Ser Arg Glu Ala Lys Lys Gln Val Glu Lys<br>                 290                   295                  300 | 912 |
| GCT TTA GAA GAA GCA AAC AGC AAA TTA GCT GCT CTT GAA AAA CTT AAC<br>Ala Leu Glu Glu Ala Asn Ser Lys Leu Ala Ala Leu Glu Lys Leu Asn<br>305                     310                   315                  320 | 960 |
| AAA GAG CTT GAA GAA AGC AAG AAA TTA ACA GAA AAA GAA AAA GCT GAA<br>Lys Glu Leu Glu Glu Ser Lys Lys Leu Thr Glu Lys Glu Lys Ala Glu<br>                 325                   330                  335 | 1008 |

```
CTA CAA GCA AAA CTT GAA GCA GAA GCA AAA GCA CTC AAA GAA CAA TTA      1056
Leu Gln Ala Lys Leu Glu Ala Glu Ala Lys Ala Leu Lys Glu Gln Leu
            340                 345                 350

GCG AAA CAA GCT GAA GAA CTC GCA AAA CTA AGA GCT GGA AAA GCA TCA      1104
Ala Lys Gln Ala Glu Glu Leu Ala Lys Leu Arg Ala Gly Lys Ala Ser
            355                 360                 365

GAC TCA CAA ACC CCT GAT ACA AAA CCA GGA AAC AAA GCT CTT CCA GGT      1152
Asp Ser Gln Thr Pro Asp Thr Lys Pro Gly Asn Lys Val Leu Pro Gly
            370                 375                 380

AAA GGT CAA GCA CCA CAA GCA GGT ACA AAA CCT AAC CAA AAC AAA GCA      1200
Lys Gly Gln Ala Pro Gln Ala Gly Thr Lys Pro Asn Gln Asn Lys Ala
385                 390                 395                 400

CCA ATG AAG GAA ACT AAG AGA CAG TTA CCA TCA ACA GGT GAA ACA GCT      1248
Pro Met Lys Glu Thr Lys Arg Gln Leu Pro Ser Thr Gly Glu Thr Ala
            405                 410                 415

AAC CCA TTC TTC ACA GCG GCA CGC GTT ACT GTT ATG GCA ACA GCT GGA      1296
Asn Pro Phe Phe Thr Ala Ala Arg Val Thr Val Met Ala Thr Ala Gly
            420                 425                 430

GTA GCA GCA GTT GTA AAA CGC AAA GAA GAA AAC TAA                      1332
Val Ala Ala Val Val Lys Arg Lys Glu Glu Asn
            435                 440

(2) INFORMATION FOR SEQ ID NO:6:

(i) SEQUENCE CHARACTERISTICS:
        (A) LENGTH: 443 amino acids
        (B) TYPE: amino acid
        (D) TOPOLOGY: linear (ii) MOLECULE TYPE: protein (xi) SEQUENCE DESCRIPTION: SEQ ID NO:6:

Asn Gly Asp Gly Asn Pro Arg Glu Val Ile Glu Asp Leu Ala Ala Asn
1               5                  10                  15

Asn Pro Ala Ile Gln Asn Ile Arg Leu Arg His Glu Asn Lys Asp Leu
            20                  25                  30

Lys Ala Arg Leu Glu Asn Ala Met Glu Val Ala Gly Arg Asp Phe Lys
        35                  40                  45

Arg Ala Glu Glu Leu Glu Lys Ala Lys Gln Ala Leu Glu Asp Gln Arg
    50                  55                  60

Lys Asp Leu Glu Thr Lys Leu Lys Glu Leu Gln Gln Asp Tyr Asp Leu
65                  70                  75                  80

Ala Lys Glu Ser Thr Ser Trp Asp Arg Gln Arg Leu Glu Lys Glu Leu
                85                  90                  95

Glu Glu Lys Lys Glu Ala Leu Glu Leu Ala Ile Asp Gln Ala Ser Arg
            100                 105                 110

Asp Tyr His Arg Ala Thr Ala Leu Glu Lys Glu Leu Glu Glu Lys Lys
        115                 120                 125

Lys Ala Leu Glu Leu Ala Ile Asp Gln Ala Ser Gln Asp Tyr Asn Arg
    130                 135                 140

Ala Asn Val Leu Glu Lys Glu Leu Glu Thr Ile Thr Arg Glu Gln Glu
145                 150                 155                 160

Ile Asn Arg Asn Leu Leu Gly Asn Ala Lys Leu Glu Leu Asp Gln Leu
                165                 170                 175

Ser Ser Glu Lys Glu Gln Leu Thr Ile Glu Lys Ala Lys Leu Glu Glu
            180                 185                 190

Glu Lys Gln Ile Ser Asp Ala Ser Arg Gln Ser Leu Arg Arg Asp Leu
        195                 200                 205
```

```
Asp Ala Ser Arg Glu Ala Lys Lys Gln Val Glu Lys Asp Leu Ala Asn
    210                 215                 220

Leu Thr Ala Glu Leu Asp Lys Val Lys Glu Asp Lys Gln Ile Ser Asp
225                 230                 235                 240

Ala Ser Arg Gln Arg Leu Arg Arg Asp Leu Asp Ala Ser Arg Glu Ala
                245                 250                 255

Lys Lys Gln Val Glu Lys Asp Leu Ala Asn Leu Thr Ala Glu Leu Asp
            260                 265                 270

Lys Val Lys Glu Glu Lys Gln Ile Ser Asp Ala Ser Arg Gln Arg Leu
        275                 280                 285

Arg Arg Asp Leu Asp Ala Ser Arg Glu Ala Lys Lys Gln Val Glu Lys
    290                 295                 300

Ala Leu Glu Glu Ala Asn Ser Lys Leu Ala Ala Leu Glu Lys Leu Asn
305                 310                 315                 320

Lys Glu Leu Glu Glu Ser Lys Lys Leu Thr Glu Lys Glu Lys Ala Glu
                325                 330                 335

Leu Gln Ala Lys Leu Glu Ala Glu Ala Lys Ala Leu Lys Glu Gln Leu
            340                 345                 350

Ala Lys Gln Ala Glu Glu Leu Ala Lys Leu Arg Ala Gly Lys Ala Ser
        355                 360                 365

Asp Ser Gln Thr Pro Asp Thr Lys Pro Gly Asn Lys Ala Val Pro Gly
    370                 375                 380

Lys Gly Gln Ala Pro Gln Ala Gly Thr Lys Pro Asn Gln Asn Lys Ala
385                 390                 395                 400

Pro Met Lys Glu Thr Lys Arg Gln Leu Pro Ser Thr Gly Glu Thr Ala
                405                 410                 415

Asn Pro Phe Phe Thr Ala Ala Arg Val Thr Val Met Ala Thr Ala Gly
            420                 425                 430

Val Ala Ala Val Val Lys Arg Lys Glu Glu Asn
        435                 440

(2) INFORMATION FOR SEQ ID NO:7:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:7:

GCTCAGGCGG CGCCGGTAGA AAATAAAGAA GAAACACCAG AAAC                44

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:8:

Val Glu Asn Lys Glu Glu Thr Pro Glu
1               5

(2) INFORMATION FOR SEQ ID NO:9:

(i) SEQUENCE CHARACTERISTICS:
        (A) LENGTH: 47 base pairs
        (B) TYPE: nucleic acid
        (C) STRANDEDNESS: single
        (D) TOPOLOGY: linear
```

(xi) SEQUENCE DESCRIPTION: SEQ ID NO:9:

CAGCAGCAGG ATTCTTATTA TTCTTCTGGT TTTTCGTCAA CTTTCTT                47

(2) INFORMATION FOR SEQ ID NO:10:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:10:

CAGCAGCAGC CATGGGTTCT TCTGGTTTTT CGTCAACTTT CTTA                   44

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:11:

GGCCATGGAC ACTTACAAAT TAATCCTTAA TGGT                              34

(2) INFORMATION FOR SEQ ID NO:12:

(i) SEQUENCE CHARACTERISTICS:
        (A) LENGTH: 10 amino acids
        (B) TYPE: amino acid
        (C) STRANDEDNESS:
        (D) TOPOLOGY: linear (xi) SEQUENCE DESCRIPTION: SEQ ID NO:12:

Met Asp Thr Tyr Lys Leu Ile Leu Asn Gly
1               5                   10

(2) INFORMATION FOR SEQ ID NO:13:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:13:

CAGGTCGACT TATTACATTT CAGTTACCGT AAAGGTCTTA GT                     42

(2) INFORMATION FOR SEQ ID NO:14:

(i) SEQUENCE CHARACTERISTICS:
        (A) LENGTH: 152 base pairs
        (B) TYPE: nucleic acid
        (C) STRANDEDNESS: single
        (D) TOPOLOGY: linear (xi) SEQUENCE DESCRIPTION: SEQ ID NO:14:

AAGCTTAAGG AGGTTAATCG ATGAAAAAAA CTGCTATCGC TATCGCTGTT GCTCTGGCTG     60

GTTTCGCTAC TGTTGCTCAG GCGGCGCCGA GATCTAAACA GGAATTCGAG CTCGGTACCC    120

GGGGATCCTC TAGAGCTGAC CTGCAGGCAT GC                                  152

PROTEIN L AND HYBRID PROTEINS THEREOF

CROSS-REFERENCE TO RELATED APPLICATIONS

This application is a division of U.S. patent application Ser. No. 08/325,278, filed Oct. 26, 1994 pending; which application is a National Phase filing under 35 U.S.C. 371 and 37 C.F.R. 1.494 or 1.495 of PCT Application No. PCT/SE93/00375, filed Apr. 28, 1993; which application claims priority from Swedish Application No. 9201331-7, filed Apr. 28, 1992.

TECHNICAL FIELD

The present invention relates to sequences of protein L which bind to light chains of immunoglobulins. The invention also relates to hybrid proteins of protein L having the ability to bind to light chains of all Ig and also to bind to light and heavy chains of immunoglobulin G, DNA-sequences which code for the proteins vectors that contain such DNA-sequences, host cells transformed by the vectors, methods for preparing the proteins, reagent apparatus for separating and identifying immunoglobulins, compositions and pharmaceutical compositions which contain the proteins.

BACKGROUND OF THE INVENTION

The invention relates in particular to the DNA-sequence and to the amino acid sequence of the light-chain forming domains of protein L.

Proteins which bind to the constant domains (of high affinity) of the immunoglobulins (Ig) are known. Thus, protein A (from *Staphylococcus aureus*) (Forsgren, A. and Sjöquist, J. (1966) Protein A from *Staphylococcus aureus*. I. Pseudo-immune reaction with human gammaglobulin. J. Immunol. 97: 822–827) binds to IgG from various mammal species. The binding of protein A to IgG is mediated essentially via surfaces in the Fc-fragment of the heavy chain of the IgG-molecule, although a certain bond is also effected with surfaces in the Fab-fragment of the IgG. Protein A lacks the ability of binding to human IgG3 and neither will it bind to IgG from several other animal species, such as important laboratory animals, for instance rats and goats, which limits the use of protein A.

Protein G (Björck, L. and Kronvall, G. (1984) Purification and some properties of streptococcal protein G, a novel IgG-binding reagent. J. Immunol. 133: 969–974; Reis, K., Ayoub, E. and Boyle, M. (1984) Streptococcal Fc receptors. I. Isolation and partial characterization of the receptor from a group C streptococcus. J. Immunol. 132: 3091–3097) binds to heavy chains in human IgG and to all four of its subclasses and also to IgG from most mammals, including rats and goats.

Protein H (Åkesson, P., Cooney, J., Kishimoto, F. and Björck, L. (1990) Protein H—a novel IgG binding bacterial protein. Molec. Immun. 27: 523–531) binds to the Fc-fragment in IgG from human beings, monkeys and rabbits. However, the bond is weaker than in the case of protein G and A, which may be beneficial when wishing to break the bond with a weak agent, for instance when purifying proteins which are readily denatured with the aid of antibodies.

Protein M (Applicant's Patent Application PCT/SE 91100447) binds to the Fc-fragment in IgG from humans, monkeys, rabbits, goats, mice and pigs.

Protein L (Björck, L. (1988) Protein L, a novel bacterial cell wall protein with affinity to Ig L chains. J. Immunol. 140: 1194–1197), which binds to the light chains in immunoglobulins from all of the classes G, A, M, D and E is known (U.S. Pat. No. 4,876,194). The amino acid sequence and the binding domains of this protein, however, have hitherto been unknown.

The aforesaid proteins can be used in the analysis, purification and preparation of antibodies and for diagnostic and biological research.

The elimination of immunoglobulins, with the aid of plasmapheresis, can have a favorable effect on some autoimmune diseases. A broadly binding protein would be an advantage when wishing to eliminate all classes of antibodies in this context.

It has long been known that infectious conditions can be prevented or cured with the introduction of an immune serum, i.e. a serum which is rich in antibodies against the organism concerned or its potentially harmful product. Examples hereof are epidemic jaundice, tetanus, diphtheria, rabies and generalized shingles. Antibodies against a toxic product may also be effective in the case of non-infectious occasioned conditions. Serum produced in animals against different snake venoms is the most common application in this respect. However, the administration of sera or antibody preparations is not totally without risk. Serious immunological reactions can occur in some cases. Singular cases of the transmission of contagious diseases, such as HIV and hepatitis through the agency of these products have also been described. In order to avoid these secondary effects, it has been desirable to produce therapeutic antibodies in test tubes. A large number of novel techniques for the preparation of antibodies in test tubes have been proposed in recent years. Examples of such techniques are hybridom techniques, synthesis of chima-antibodies and the preparation of antibodies in bacteria. These techniques also enable antibodies to be specially designed which can further widen the use of such molecules as therapeutics, for instance in the case of certain tumour-diseases. In the case of some of these novel methods, however, the product totally lacks the Fc-fragment to which all of the described IgG-binding proteins, with the exception of protein L, bind. There is consequently a need of a process for purifying antibodies for therapeutic use, wherein proteins which have a broad binding activity/specificity, can be of value.

It has long been possible to utilize the antibody reaction with its high grade specificity for diagnosing past or, in some cases, ongoing infections with different parasites. This indirect method of indicating infectious agents is called serology and, in many cases, may be the only diagnostic alternative. In certain cases, it can also be of interest to exhibit specific IgE- or IgA-antibodies. When diagnosing with the aid of serology, the antigen is most often fastened to a solid phase, whereafter serum taken from the patient is incubated with the antigen. Antibodies that have been bound from the patient can then be detected in different ways, often with the aid of a secondary antibody (for instance, an antibody which is directed against the light chains of human antibodies) to which an identifiable label has been attached, such as alkaline phosphatase, biotin, radioactive isotopes, fluorescein, etc. In this context, a protein having a broad Ig binding capacity can be used as an alternative to secondary antibodies.

There are a number of non-therapeutic and non-diagnostic reasons for the necessity to bind antibodies. Antibodies are often used in research, both for detection and for purifying the antigen against which they are directed. All techniques which facilitate the purification of antibodies and, in particular, techniques which enable different classes to be purified, are of interest in this context.

Consequently, there is a serious need of a protein which has a broad binding activity/specificity and which binds to several different classes of immunoglobulins from different animal species. At present, there is no known protein which will bind to all immunoglobulin classes. The earlier known proteins A, G, H and M bind only to heavy chains in IgG. The known protein L (Björck et al, 1988) binds to the light χ-chains and γ-chains in immunoglobulins of all classes, although the bonds are much weaker on the κ-chains. Applicant has charted protein L, has determined the amino acid sequence for protein L, has identified the light-chain binding domains on protein L, and has used these to produce hybrid proteins which possess the IgG-Fc-binding domains of protein G. The Applicant is able to show through protein LG that a protein of broader binding activity/specificity can be produced thereby. The aforesaid proteins A, G, H and M bind to the same surfaces, or to very closely lying surfaces on IgG-Fc. The protein L which binds to light chains can thus be combined with any other functionally similar protein which binds to the Fc-fragment of heavy chains. A similar broadening of the Ig-binding activity is achieved with all alternatives.

DETAILED DESCRIPTION OF THE INVENTION

Thus, the present invention relates to the sequence of protein L which binds to light chains in Ig and has the amino acid sequence disclosed in FIG. 1, and variants, subfragments, multiples or mixtures of the domains B1–B5 having the same binding properties. The invention also relates to a DNA-sequence which codes for such protein sequences, for instance the DNA-sequence in FIG. 1.

The invention is concerned with a hybrid protein which is characterized by comprising domains which bind to the light χ-chains and λ-chains in immunoglobulins of all classes, and also comprises domains which bind to heavy chains in immunoglobulin G, wherein those domains which bind to the light chains are chosen from among the B1-, B2-, B3-, B4- and B5-domains in protein L and those domains which bind to heavy chains of immunoglobulins are chosen from the C1-, C2- and C3-domains in protein G; the A-, B- and C1-domains from protein H; the A-, B1-, B2- and S-domains in protein M1 or the E-, D-, A-, B- and C-domains in protein A (see FIG. 6) and variants, subfragments, multiples or mixtures of these domains that have the same binding properties which bind to heavy chains of immunoglobulins.

By subfragment is meant a part-fragment of the given domains or fragments which include parts from the various domains having mutually the same binding properties. By variants is meant proteins or peptides in which the original amino acid sequence has been modified or changed by insertion, addition, substitution, inversion or exclusion of one or more amino acids, although while retaining or improving the binding properties. The invention also relates to those proteins which contain several arrays (multiples) of the binding domains or mixtures of the binding domains with retained binding properties. The invention also relates to mixtures of the various domains of amino acid sequences having mutually the same binding properties.

The invention relates in particular to a hybrid protein designated LG, and is characterized in that the hybrid protein includes the B-domains in protein L which bind to the light chains in immunoglobulins, and the C1-domains and C2-domains in protein G which bind to heavy chains and have the amino acid sequence disclosed in FIG. 3. The invention also relates to variants, subfragments, multiples or mixtures of these domains.

Protein LG is a hybrid protein having a molecular weight of about 50 kDa (432 amino acids) and comprising four domains, each of which binds to light chains in immunoglobulins, and two IgG-binding domains from protein G. The hybrid protein combines a broad IgG-binding activity, deriving from the high-grade binding ability of protein G to the Fc-fragment of the heavy chain on IgG with the ability of the protein L to bind to light chains of all classes of immunoglobulins. Thus, protein LG binds polyclonal human IgG, IgM, IgA, IgD and IgE. The affinity for human polyclonal IgG is $2 \times 10^{10} M^{-1}$. All four human immunoglobulin classes are bound. Binding to human IgG is effected with both the κ-and the λ-chain. Both the Fc-fragment and the Fab-fragment of IgG are bound to the hybrid protein. The protein also binds human IgA-, IgD-, IgE- and IgM-antibodies. The bond is stronger to human immunoglobulins which carry χ than to those which carry the λ-isotope of light chains. IgG from most mammals will be bound by protein LG, thus also IgG from goats and cows, which do not bind to protein L. However, rabbit-IgG which binds relatively weakly to protein L will bind well to the fusion protein. IgM and IgA-antibodies from mice, rats and rabbits will be bound to the protein.

Protein LG is highly soluble. It is able to withstand heat and will retain its binding properties even at high temperatures. The binding properties also remain in a broad pH-range of 3–10. The protein withstands detergent and binds marked or labelled proteins subsequent to separation in SDS-PAGE and transference to membranes with elektroblotting. The protein can be immobilized on a solid phase (nitrocellulose, Immobilon®, polyacrylamide, plastic, metal and paper) without losing its binding capacity. The binding properties are not influenced by marking with radioactive substances, biotin or alkaline phosphatase. (The binding abilities of the protein LG are disclosed in Example 3).

The protein comprises 432 amino acids and has a molecular weight of 50 kDa deriving therefrom. The sequence is constructed of an ala sequence of the three last amino acids in the A-domain of the protein L (val-glu-asn), this ala sequence being unrelated to the two proteins, whereafter the four mutually high-grade homologous B-domains from protein L follow. The first of the B-domains is comprised of 76 amino acids, and the remaining domains are each comprised of 72 amino acids. The first nine amino acids from the fifth B-domain are included and followed by two non-related amino acids (pro-met). The protein G-sequences then follow. The last amino acid in the so-called S-domain from protein G is followed by an IgG-binding domain from protein G (C1; 55 amino acids), the intermediate D-region (15 amino acids) and the second IgG-binding C-domain (C2; 55 amino acids). The last amino acid is a methionine, which occurs in natural protein G as the first amino acid in the so-called W-region.

The invention also relates to DNA-sequences which code for the aforesaid proteins.

The gene which codes for the IgG-binding amino acid sequences can be isolated from the chromosomal DNA from *Staphylococcus aureus* based on the information on the DNA-sequence for protein A (S. Löfdahl, B. Guss, M. Uhlen, L. Philipsson and M. Lindberg. 1983. Gene for staphylococcal protein A. Proc. Natl. Acad. Sci. USA. 80: 697–701) and FIG. 6, or from G-streptococcus, preferably strain G 148 or C-streptococcus, preferably strain Streptococcus equisimilis C 40, based on the information on protein G (B. Guss, M. Eliasson, A. Olsson, M. Uhlen, A.-K. Frej, H. Jörvall, I. Flock and M. Lindberg. 1986. Structure of the IgG-binding regions of streptococcal protein G. EMBO. J. 5: 1567–1575) and FIG. 6, or from group A-streptococcus, e.g. *S. pyogenes* (type M1) based on the information on the DNA-sequence for protein H (H. Gomi, T. Hozumi, S. Hattori, C. Tagawa, F. Kishimoto and L. Björck. 1990. The gene sequence and some properties of protein H—a novel IgG binding protein J. Immunol. 144: 4046–4052) and FIG. 6, or from the chromosomal DNA in group A-streptococcus type M1 based on the information on the DNA-sequence for protein M (Applicant's Patent Application, PCT/SE 91100447) and FIGS. 6 and 7. The gene which codes for the protein that binds to light chains can be isolated from the chromosomal DNA from *Peptostreptococcus magnus* 312 based on the information on the DNA-sequence for protein L in FIG. 2.

By using the chromosomal DNA obtained from the aforesaid bacteria as a template, a DNA-fragment defined with the aid of two synthetic oligonucleotides can then be specifically amplified with the aid of PCR (Polymerase Chain Reaction). This method also enables recognition sites to be incorporated for restriction enzymes in the ends of the amplified fragments (PCR technology, Ed: PCR Technology. Principles and Applications for DNA Amplification. Ed. Henry Erlich. Stockton Press, New York, 1989). The choice of recognition sequences can be adapted in accordance with the vector chosen to express the fragment or the DNA-fragment or other DNA-fragments with which the amplified fragment is intended to be combined. The amplified fragment is then cleaved with the restriction enzyme or enzymes concerned and is combined with the fragment/the other fragments concerned and the fragments are then cloned together in the chosen vector (in this case, the expression vector) (Sambrook, J. E. Fritsch and T. Maniatis, 1989, Molecular cloning: A laboratory manual, 2nd Ed. Cold Spring Harbor Laboratories, Cold Spring Harbor, N.Y., USA). The plasmid vector pHD313 can be used (Dalböge, H. E. Bech Jensen, H. Töttrup, A. Grubb, M. Abrahamson, I. Olafsson and S. Carlsen, 1989. High-level expression of active human cystatin C in *Escherichia coli*. Gene, 79: 325–332), alternatively one of the vectors in the so-called PET-series (PET 20, 21, 22, 23) retailed by Novagen (Madison, Wis., USA).

The hybrid proteins are then incorporated in an appropriate host, preferably *E. coli*. The invention also relates to such hosts as those in which the hybrid proteins are incorporated.

Those clones which produce the desired proteins can be selected from the resultant transformants with the aid of a known method (Fahnestock et al., J. Bacteriol. 167, 870 (1986).

When the proteins that can bind to the light chains in the immunoglobulins and to the heavy chains in IgG have been purified from the resultant positive clones with the aid of conventional methods, the binding specificities of the proteins are determined for selection of those clones which produce a protein that will bind to the light chains in immunoglobulins and to the heavy chains in IgG.

Subsequent to having isolated plasmid DNA in said clone with conventional methods, the DNA-sequence in the inserted material is determined with known methods (Sanger et al., Proc. Natl. Acad. Sci. USA 74, 5463 (1977).

The invention also relates to DNA-sequences which hybridize with said identified DNA-sequences under conventional conditions and which code for a protein that possesses the desired binding properties. Strict hybridizing conditions are preferred.

Expression of the genes can be effected with expression vectors which have the requisite expression control regions, the structural gene being introduced after said regions. As illustrated in FIG. 1 and Claim 2, the structural gene can be used for protein LG or other hybrid proteins with protein L.

With regard to expression vectors, different host-vector-systems have been developed, of which the most suitable host-vector-systems can be selected for expression of the genes according to the present invention.

The present invention also relates to a method of producing the inventive hybrid proteins by cultivating a host cell which is transformed with an expression vector in which DNA't which codes for the proteins according to the invention is inserted.

This method includes the steps of
(1) inserting into a vector a DNA-fragment which codes for the hybrid proteins;
(2) transforming the resultant vector into an appropriate host cell;
(3) cultivating the resultant, transformed cell for preparation of the desired hybrid protein; and
(4) extracting the protein from the culture.

In the first step, the DNA-fragment which codes for the hybrid protein is inserted in a vector which is suitable for the host that is to be used to express the hybrid protein. The gene can be inserted by cleaving the vector with an appropriate restriction enzyme, and then legating the gene with the vector.

In the second step, the vector with the hybrid plasmid is inserted into host cells. The host cells may be *Escherichia, coli, Bacillus subtilis* or *Saccharomyces cerevisiae* or other suitable cells. Transformation of the expressions hybrid vector into the host cell can be effected in a conventional manner and clones which have been transformed can then be selected.

In the third step, the obtained transformants are cultivated in an appropriate medium for preparation of the desired proteins by expression of the gene coded for the hybrid protein.

In the fourth step, the desired protein is extracted from the culture and then purified. This can be achieved with the aid of known methods. For instance, the cells can be lysed with the aid of known methods, by treating the cells with ultrasonic sound, enzymes or by mechanical degradation. The protein which is released from the cells or which excretes in the medium can be recovered and purified with the aid of conventional methods often applied within the biochemical field, such as ion-exchange chromatography, gel filtration, affinity chromatography with the use of immunoglobulins as ligands, hydrophobic chromatography or reverse-phase chromatography. These methods can be applied individually or in suitable combinations.

As before mentioned, the inventive proteins may be used for binding, identifying or purifying immunoglobulins. They can also be bound to pharmaceuticals and used in formulations which have delayed release properties. To this end, the protein may be present in a reagent appliance for pharmaceutical composition in combination with appropriate reagents, additives or carriers.

The proteins can be handled in a freeze-dried state or in a PBS-solution (phosphate-buffered physiological salt solution) pH 7.2 with 0.02% $NaN_3$. It can also be used connected to a solid phase, such as carbohydrate-based phases, for instance CNBr-activated sepharose, agarose, plastic surfaces, polyacrylamide, nylon, paper, magnetic spheres, filter, films. The proteins may be marked with biotin, alkaline phosphatase, radioactive isotopes, fluorescein and other fluorescent substances, gold particles, ferritin, and substances which enable luminescence to be measured.

Other proteins may also be used as carriers. These carriers may be bound to or incorporated in the proteins, in accordance with the invention. For instance, it is conceivable to consider the whole of proteins A, G, H, M as carriers for inserted sequences of protein L which bind to light chains. In turn, these carriers can be bound to the aforesaid carriers.

The pharmaceutical additions that can be used are those which are normally used within this field, such as pharmaceutical qualities of mannitol, lactose, starch, magnesium stearate, sodium saccharate, talcum, cellulose, glycose, gelatine, saccharose, magnesium carbonate and similar extenders, such as lactose, dicalcium phosphate and the like; bursting substances, such as starch or derivatives thereof; lubricants such as magnesium stearate and the like; binders, such as starch, gum aribicum, polyvinylpyrrolidone, gelatine, cellulose and derivatives thereof, and the like.

BRIEF DESCRIPTION OF THE DRAWINGS

The invention will now be described in more detail with reference to the accompany drawings, in which FIG. 1 illustrates the plasmid pHD389; the ribosomal binding sequence, the sequence for the signal peptide from ompA and recognition sequence for several restriction enzymes are shown (SEQ ID No: 14);

FIG. 2 illustrates the amino acid and nucleic acid sequence for protein LG (SEQ ID Nos: 3 and 4 respectively);

FIGS. 5a, 5b and 5c are schematic overall views of the production of the hybrid proteins LA, LM and LH respectively;

FIG. 7 illustrates the amino acid and nucleic acid sequence for protein M1 (SEQ ID Nos: 6 and 5 respectively);

Figure 3A:
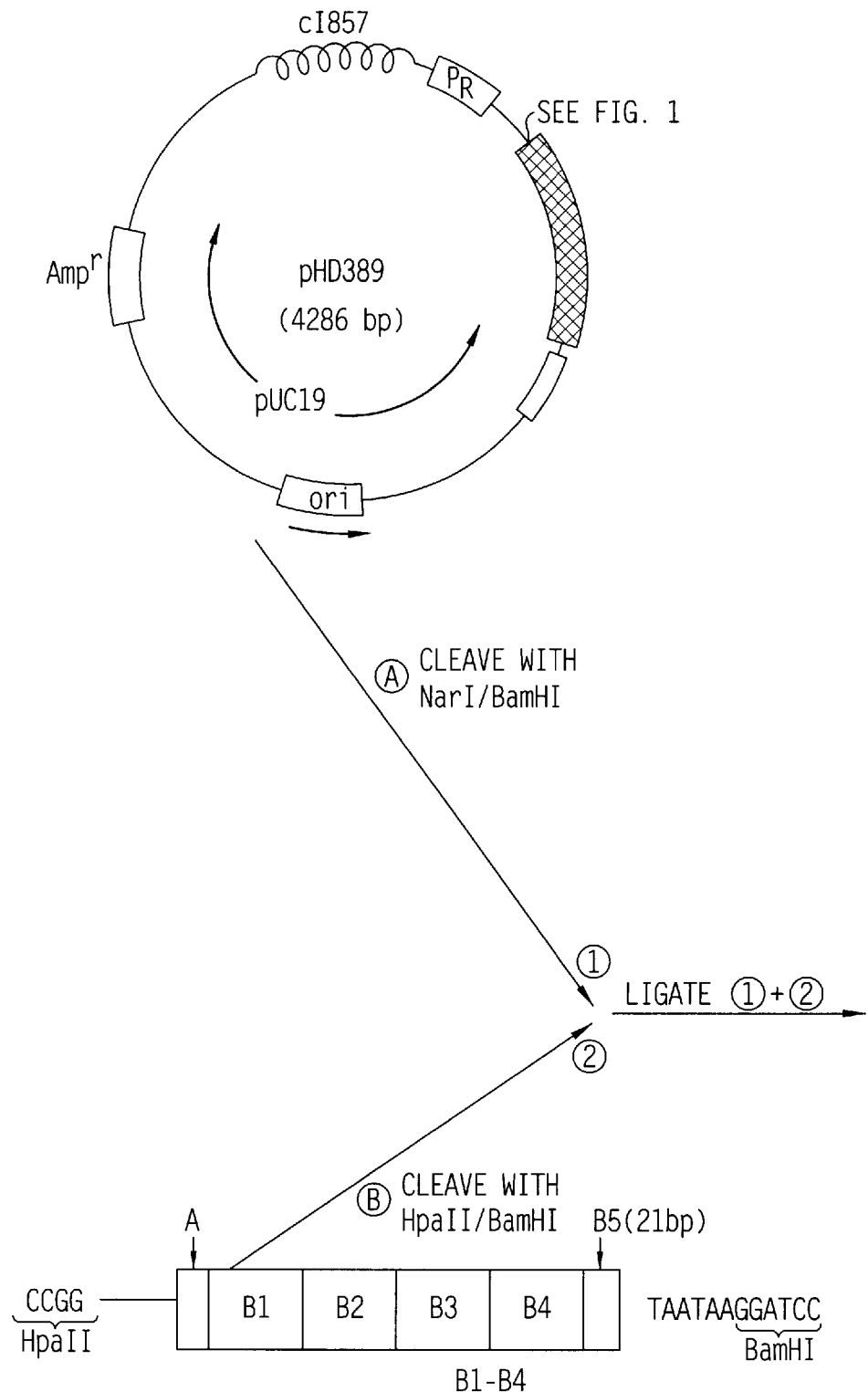
FIG. 3 is a schematic overall view of the production of protein L.
Figure 3B:
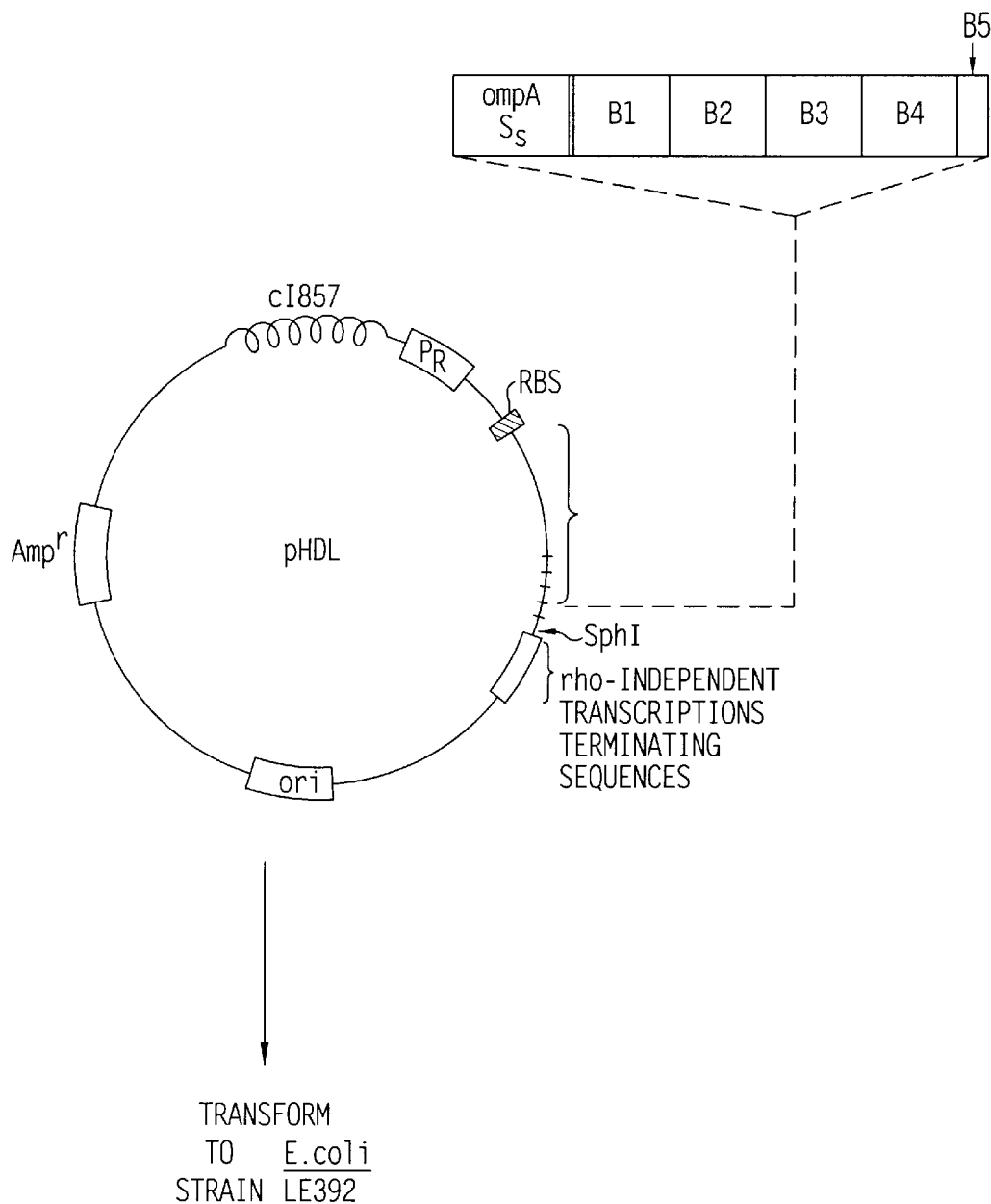
Figure 4A:
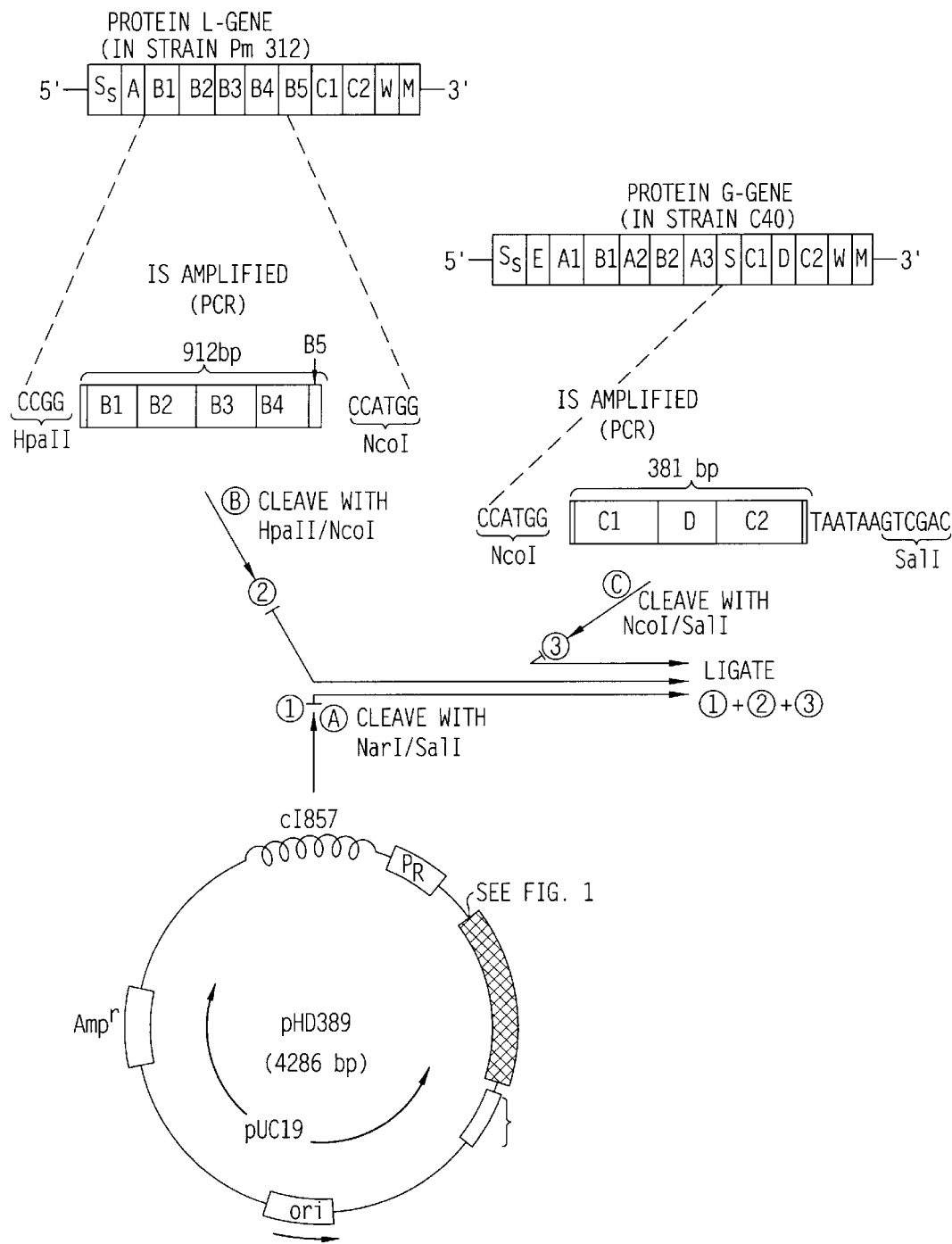
FIG. 4 is a schematic overall view of the production of protein LG.
Figure 4B:
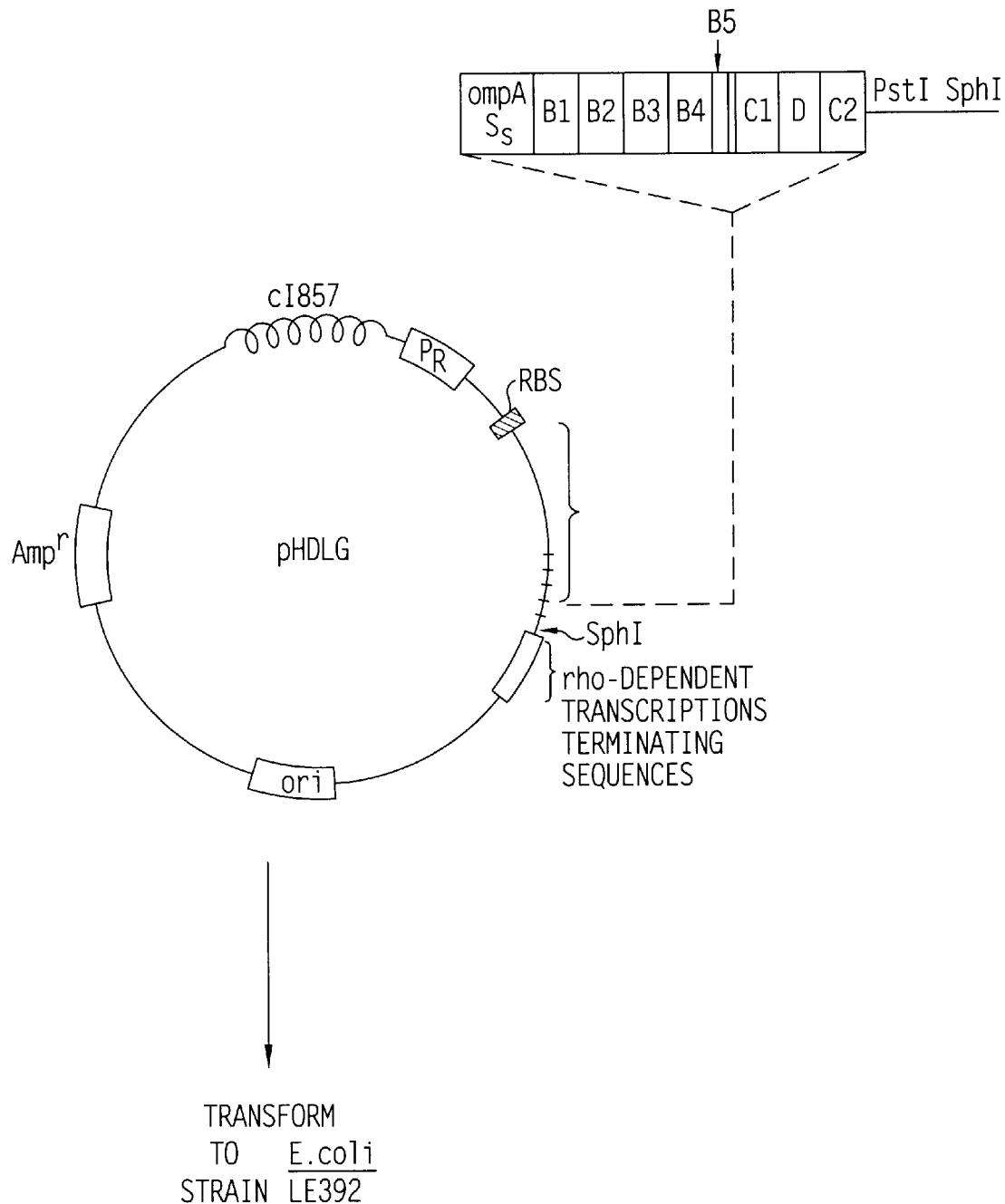
Figure 6:
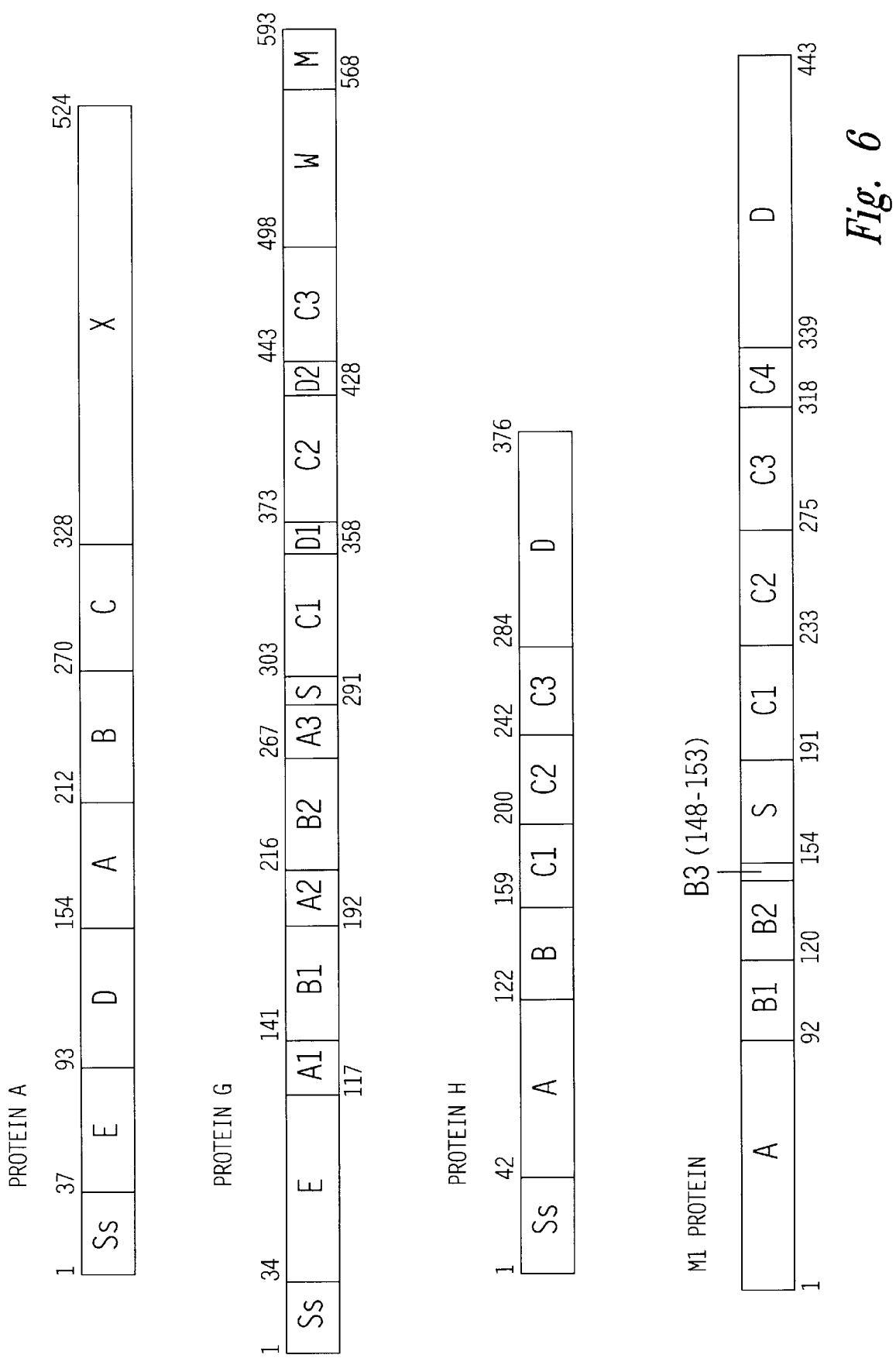
FIG. 6 is a schematic inclusive illustration of protein A, G, H and M1. IgGFc-binding domains are for protein A: E, D, A, B and C; for protein G: C1, C2 and C3; for protein H: A and/or B; and for protein M1: A, B1, B2, B3 and S.

The amino acid and nucleic acid sequence of the light-chain binding domains of protein L (SEQ ID Nos: 1 and 2 respectively) is illustrated in FIG. 2.

It will be observed that the drawings are not to scale.

EXAMPLE 1

Cloning and Expression of the IgG-light-chain-binding Domains in Protein L

Construction of Synthetic Oligonucleotides (primers) for Amplifying Sequences Coded for Protein L, Domain B1–B4

It has been found that a protein L peptide (expressed in *E. coli*) constructed of the sequence ala-val-glu-asn-domain B1 (from protein L) binds to the light chains of the immunoglobulins (W. Kastern, U. Sjöbring and L. Björck. 1992. Structure of peptostreptococcal protein L and identification of a repeated immunoglobulin light chain-binding domain. J. Biol. Chem. in-print). Since this simple protein L-domain has a relatively low affinity to Ig, $(1\times10^7 M^{-1})$, and since the naturally occurring protein L which is constructed of several mutually similar domains (B1–B5) has a high affinity to Ig $(1\times10^{10} M^{-1})$ four of these domains have been expressed together in the following way:

PL-N and PL-C1 are synthetic oligonucleotides (manufactured by the Biomolecular Unit at Lund University (Sweden) in accordance with Applicant's instructions) which have been used to amplify a clonable gene fragment which is amplified with PCR (Polymerase Chain Reaction) and which codes for four Ig-binding protein L domains (ala-val-glu-asn-B1-B2-B3-B4-lys-lys-val-asp-glu-lys-pro-glu-glu). Amino acids in the protein L-sequence are given for the primer which corresponds to the coded strand (PL-N) (SEQ ID Nos: 7 and 8):

PL-N:
5'-GCTCAGGCGGCGCCGGTAGAAAATAAAGAAGAAACACCAGAAAC-3'
                              valgluasnlysgluglulthrproglu 5'-end of this oligonucleotide is homologous with the coded strand in the protein L-gene (emphasized): those codons which code for the last three amino acids in the A-domain (val-glu-asn) are followed by the codons for the first six amino acids in the first of the Ig-binding domains in protein L (B1).

PL-C1: 5'-CAGCAGCAGGATTC TTATTATTCTTCTGGTTTTTCGTCAACTTT CTT-3' (SEQ ID No: 9)

This oligonucleotide is homologous with the opposing non-coding strand in the gene for protein L (the sequence corresponds to the first nine amino acids in domain B5).

DNA-fragments which have been amplified with the aid of PL-N contain the recognition sequence for the restriction enzyme HpaII (emphasized) immediately before the codon which is considered to code for the first amino acid (val) in the expressed protein L-fragment. The fragment which is cleaved with HpaII can be ligated with DNA (in this case, consisting of the used expression vector pHD389) which has been cleaved with the restriction enzyme NarI. The DNA-fragment that has been cleaved with HpaII and ligated with vector pHD389, which has been cleaved with NarI, will be translated in the correct reading frame. The construction results in translation of an additional amino acid (ala) immediately in front of the first amino acid in protein L.

DNA-fragments which have been amplified with the aid of PL-C1 will contain the recognition sequence for the restriction enzyme BamHI (overlined above the sequence) immediately after the sequence which codes for the last amino acid in the expressed protein L-fragment (glu). The vector pHD389 contains a unique recognition sequence for BamHI as part of its so-called multiple cloning sequence which follows the NarI recognition sequence. DNA-fragments which have been amplified with the aid of PL-C1 will include two so-called stop-codons (emphasized) which results in translation of the fragment inserted in the vector to cease.

The sequence which was considered to be amplified contains no internal recognition sequences for the restriction enzymes HpaII or BamHI.

Amplifying and Cloning Procedures (PCR) (Polymerase Chain Reaction) was effected with a protocol described by Saiki, R. D. Gelfand, S. Stoffel, S. Scharf, R. Higuchi, G. Horn, K. Mullis and H. Erlich, 1988; Primer-directed enzymatic amplification of DNA with a thermostable DNA polymerase. Science 239: 487–49127; PCR was effected in a Hybaid Intelligent Heatingblock (Teddington, UK): 100 μl of a reaction mixture contained 50 mM KCl, 10 mM Tris-HCl, pH 8.3, 1.5 mM MgCl$_2$, 100 μ/ml gelatine, 300 μM with respect to each of the deoxy-nucleotides (dATP, dCTP, dGTP, dTTP), (Pharmacia), 20 pmol of each of the oligonucleotides PL-N and PL-C1, 10 μl of a target (template) DNA-solution containing 0.1 mg/ml of chromosomal DNA from Peptostreptococcus magnus, species 312. The mixture was covered with mineral oil (Sigma) and DNA't was denatured by heating to 98° C. for 10 minutes. 2.5 units of AmpliTaq (Perkin Elmer Cetus, Norwalk, Conn.) were added and PCR was then carried out with 25 cycles consisting of a denaturing step at 94° C. for 1 minute, followed by a hybridizing step at 56° C. for 1 minute, and finally by an extension step at 72° C. for 1 minute. Amplified DNA was analyzed by electrophoresis in agarose gel. The amplified DNA't was cleaved with the restriction enzymes HpaII (Promega), (8 units/μg amplified DNA) and BamHI (Promega), (10 units/μg amplified DNA) at 37° C. The thus amplified and subsequently cleaved DNA-product was isolated by electrophoresis in a 2% (weight by volume) agarose gel (NuSieve agarose, FMC Biproducts) in a TAE-buffer (40 Mm Tris, 20 Mm Na-acetate, 2 Mm EDTA, Ph 8.0). The resulting 930 base-pair large fragment was cut from the gel. The DNA concentration in this removed gel-piece was estimated to be 0.05 mg/ml. The agarose-piece containing the cleaved, amplified fragment was melted in a water bath at 65° C., whereafter the fragment was allowed to cool to 37° C. 10 μl (0.5 μg) of this DNA was transferred to a semimicrotube (Sarstedt) preheated to 37° C., whereafter 1 μl of the vector pHD389 was immediately added and cleaved with NarI (Promega) and BamHI, 1 μl 10×ligas-buffer (Promega and 1 μl T4 DNA-ligase (Promega; 1 unit/μl). The ligating reaction was then used to transform E. coli, strain LE392, which had been competent in accordance with the rubidium/calcium-chloridemethod as described by Kushner (1978). Molecular biological standard methods have been used in the manipulation of DNA (Sambrook, J. E. Fritsch and T. Maniatis, 1989. Molecular cloning: A laboratory manual. 2nd Ed. Cold Spring Harbor Laboratories, Cold Spring Harbor, N.Y., USA). The cleaving and ligating conditions recommended by the manufacturer of DNA-ligase and restriction enzymes have been followed in other respects.

Expression System

The vector pHD389 (see FIG. 2) is a modified variant of the plasmid pHD313 (Dalböge, H. E. Bech Jensen, H. T öttrup, A. Grubb, M. Abrahamson, I. Olafsson and S. Carlsen, 1989. High-level expression of active human cystatin C in Escherichia coli. Gene, 79: 325–332). The vector, which is replicated in E. coli (contains ori=origin of replication from plasmid pUC19) is constructed so that DNA-fragments which have been cloned into the cleaving site of NarI will be transcribed and translated downstream of and in the immediate vicinity of the signal peptide (21 amino acids), from envelope-protein ompA from E. coli. Translation will be initiated from the codon ATG which codes for the first amino acid (methionine) in the signal peptide. This construction permits the translated peptide to be transported to the periplasmic space in E. coli. This is advantageous, since it reduces the risk of degradation of the desired product of enzymes occurring intracellularly in E. coli. Moreover, it is easier to purify peptides which have been exported to the periplasic space. Unique recognition sequences (multiple cloning sequences) for several other restriction enzymes, among them ecoRI, SalI and BamHI are found immediately after the NarI cleaving site. An optimized so-called Shine-Dalgarno-sequence (also called ribosomal binding site, RBS) is found seven nucleotides upstream from the ATG-codon in the signal sequence from ompA, this optimized sequence binding to a complementary sequence in 16S rRNA in the ribosomes and is responsible for the translation being initiated in the correct place. The transcription of such DNA as that which is co-transcribed with the signal sequence for ompA is controlled by the $P_R$-promotor from coliphage λ. The vector also contained the gene for cI857 from coliphage λ whose product down-regulates transcription from $P_R$ (and whose product is expressed constitutively). This cI857-mediated down-regulation of transcription from $P_R$ is heat-sensitive. The transcription regulated from this promotor is terminated with the aid of a so-called rho-independent transcription terminating sequence (forms a structure in DNA't which results in the DNA-dependent RNA-polymerase leaving the DNA-strand) which is placed in the vector immediately downstream of the multiple cloning sequence. The plasmid also carries the β-lactamase gene (from the plasmid pUC19) whose product permits ampicillin-selection of E. coli clones that have been transformed by the vector.

Selection of Protein L-producing Clones

The transformed bacteria are cultivated, or cultured, on culture plates with an LB-medium which also contained ampicillin in a concentration of 100 μg/ml. Cultivation of the bacteria progressed overnight at 30° C., whereafter the bacteria were transferred to an incubator where they were cultivated for a further 4 hours at 42° C. The plates were kept in a refrigerator overnight. On the next day, the colonies were transferred to nitrocellulose filters. Filters and culture plates were marked so as to enable the transferred colonies to be readily identified on respective culture plates. The culture plates were again incubated overnight at 30° C., so that remaining rests of transferred bacteria colonies could again grow. The plates were then kept in a refrigerator.

The bacteria in the colonies on the nitrocellulose-impressions were lysed by incubating the filter in 10% SDS for 10 minutes. Filters containing lysed bacteria were then rinsed with a blocking buffer which comprised PBS (pH 7.2) with 0.25% gelatine and 0.25% Tween-20 (four baths, 250 ml each at 37° C.), whereafter the filter was incubated with radioactively marked (marked with $^{125}$I in accordance with the chloramin-T-method) Ig-κ-chains (20 ng/ml in PBS with 0.1% gelatine). The incubation took place at room temperature over a period of 3 hours, whereafter non-bound radioactively marked protein was rinsed-off with PBS (pH 7.2) containing 0.5M NaCl, 0.25% gelatine and 0.25% Tween-20 (four baths, 250 ml each at room temperature). All filters were exposed to X-ray film. Positive colonies were identified on the original culture plate. Clones which reacted with Ig-κ-chains were selected and analyzed with respect to the size on the DNA-fragment introduced in the vector. One of these clones was selected for the production of protein L, pHDL. The DNA't introduced from this clone into plasmid pHD389 was sequenced. The DNA-sequence was found to be in full agreement with corresponding sequences (B1–B4 and 21 bases in B5) in the gene for protein L from Pentostreptococcus magnus, strain 312. The size and binding properties of the protein produced by clone pHDL was analyzed with the aid of SDS-PAGE (see FIG. 8), dot-blot experiment (see FIG. 9) and competitive binding experiments.

Production of Protein L

Several colonies from a culture plate with E. coli pHDL were used to inoculate a preculture (LB-medium with an addition of 100 mg/l ampicillin), which was cultured at 28° C. overnight. On the following morning, the preculture was transferred to a larger volume (100 times the volume of the preculture) of fresh LB-medium containing ampicillin (100 mg/l) and was cultured in shake-flasks (200 rpm), (or fermentors) at 28° C. The culture temperature was raised to 40° C. (induction of transcription) when the absorbency value at 620 nm reached 0.5. Cultivation then continued for 4 hours (applied solely to cultivation in shake-flasks). Upon completion of the cultivation process, the bacteria were centrifuged down. The bacteria were then lysed with an osmotic shock method at 4° C. (Dalböge et al., 1989 supra). The lysate was adjusted to a pH=7. Remaining bacteria rests were then centrifuged down, whereafter the supernatent was purified on IgG-sepharose in accordance with earlier described protocol for protein G and protein L (U. Sjöbring, L. Björck and W. Kastern. 1991. Streptococcal protein C: Gene structure and protein binding properties. J. Biol. Chem. 266: 399–405; W. Kastern, U. Sjöbring and L. Björck. 1992. Structure of peptostreptococcal protein L and identification of a repeated immunoglobulin light chain-binding doman. J. Biol. Chem. in-print.

The expression system gave about 20 mg/l of protein L when cultivation in shake-flasks. The culture was deposited at DSSM, Identification Reference DSSM *E. coli* LE392/pHDL.

EXAMPLE 2

Cloning and Expression of Protein LG
Construction of Oligonucleotides (primers) for Amplifying Sequences which Code for Protein LG
Protein L It has been found that a protein L-peptide (expressed in *E. coli*) constructed of the sequence ala-val-glu-asn-domain B1 (from protein L) will bind to the light chains of the immunoglobulins (Kastern, Sjöbring and Björck, 1992, J. Biol. Chem. in-print). Since the affinity of this simple domain to Ig is relatively low ($1\times10^{-7}M^{-1}$) and since the naturally occurring protein L, which is comprised of several mutually similar domains (B1–B5) has a higher affinity to Ig ($1\times10^{10}M^{-1}$), four of these domains have been expressed together in the following way:

PL-N and PL-C2 are synthetic oligonucleotides (manufactured at the Biomolecular Unit at Lund University (Sweden) in accordance with Applicant's instructions) which were used, with the aid of PCR (Polymerase Chain Reaction) to amplify a clonable gene fragment, called B1-4, which codes for four Ig-binding protein L domains (alaval-glu-asn-B1-B2-B3-B4-lys-lys-val-asp-glu-lys-pro-glu-glu):

protein L-fragment. The DNA-fragment that has been amplified with the aid of PL-C2 (SEQ ID No: 10) will contain the recognition sequence for the restriction enzyme NcoI (emphasized) immediately downstream of the sequence which codes for the last amino acid in the expressed protein L-fragment (glu). Amplified fragments which have been cleaved with NcoI can be ligated to the NcoI-cleaved, PCR-generated protein-asp-CDC-met-fragment (see below).
Protein G It is known that a simple C-domain from protein G will bind to IgG (B. Guss, M. Eliasson, A. Olsson, M. Uhlen, A.-K. Frej, H. Jörnvall, I. Flock and M. Lindberg. 1986. Structure of the IgG-binding regions of streptococcal protein G. EMBO. J. 5: 1567–1575). The strength at which a simple C-domain binds to IgG is relatively low ($5\times10^{7}M^{-1}$). A fragment which consists of two C-domains with an intermediate D-region having a length of 15 amino acids, however, has a considerably higher affinity to IgG ($1\times10^{9}M^{-1}$). CDC-N and CDC-C are oligonucleotides which have been used as PCR-primers to amplify a clonable DNA-fragment, designated CDC, which codes for two IgG-binding protein G-domains (pro-met-asp-CDC-met).

CDC-N: GG$\overline{CCATGG}$ACACTTACAAATTAATCCTTAATGGT
        metaspthrtyrlysleuileleuasngly CDC-C: C$\overline{AGGTCGAC}$TTATTACATTTCAGTTACCGTAAAGGTCTTAGT Amino acids in the resultant sequence have been shown beneath the primer of the coding strand. DNA-fragments which have been amplified with the aid of CDC-N (SEQ ID Nos: 11 and 12) contain the recognition sequence for the restriction enzyme NcoI (marked with a line above the sequence). Cleaved amplified fragments can be ligated with the fragment that has been amplified with the aid of PL-C2 and then cleaved with NcoI. The fragment will therewith be translated to the correct reading frame. DNA-fragments which have been amplified with the aid of CDC-C (SEQ ID No: 13) will contain two so-called stop condons (emphasized) which terminate translation. The recognition sequence for the restriction enzyme SalI (marked with a line above the sequence) follows immediately afterwards, this sequence also being found in the expression vector pHD389 (see FIG. 1).

Those sequences which code for the binding properties of protein L (B1–B5) and for protein G (CDC) respectively contain no internal recognition sequences for the restriction enzymes HpaII, SalI or NcoI.
Amplifification and Cloning Procedures PCR (Polymerase Chain Reaction) was carried out in accordance with a protocol described by Saiki et al., 1988;

```
PL-N:    5'-GCTCAGGCGGCGCCGGTAGAAAATAAAGAAGAAACACCAGAAAC-3'
                          valgluasnlysglugluthrproglu Pl-C2:   5'-CAGCAGCAGCCATGGGTTCTTCTGGTTTTTCGTCAACTTTCTTA-3'
```

Amino acids have been shown under corresponding triplets in the coded strand. DNA-fragments which have been amplified with the aid of PL-N (SEQ ID Nos: 7 and 8) contain the recognition sequence for the restriction enzyme HpaII immediately upstream of the triplet which codes for the first amino acid (val) in the expressed protein L-fragment. The fragment that has been cleaved with HpaII can be ligated with DNA (in this case, the used expression vector pHD389) which has been cleaved with NarI. The construction results in translation of an extra amino acid (ala) immediately upstream of the first amino acid in the PCR was carried out in a Hybaid Intelligent Heating-block (Teddington, UK): 100 μl of the reaction mixture contained 50 mM KCl, 10 mM Tris-HCl, pH 8.3, 1.5 mM MgCl$_2$, 100 μg/ml gelatine, 300 μM with respect to each of the deoxy-nucleotides (dATP, dCTP, dGTP, dTTP), (Pharmacia). In order to amplify sequences which code for the light-chain binding parts of protein L, there were added 20 pmol of each of the oligonucleotides PL-N and PL-C2, and 10 μl of a DNA-solution which contained 0.1 mg/ml of chromosomal DNA from *Peptostreptococcus magnus*, strain 312. By way of an alternative, 20 pmol were added to each of the oligonucleotide pairs CDC-N and CDC-C and 10 μl of a DNA-solution which contained 0.1 mg/ml of chromosomal DNA from a group C streptococcus strain (*Streptococcus equisimilis*) called C40 (U. Sjöbring, L. Björck and W. Kastern. 1991. Streptococcal protein G: Gene structure and protein binding properties. J. Biol. Chem. 266: 399–405 or with NcoI and SalI (10 U/μg PCR-product), (for CDC) at 37° C. The thus amplified and subsequently cleaved DNA-fragments were then separated by electrophoresis in a 2% (weight by volume) agrose gel (NuSieve agarose, FMC Bioproducts) in a TAE-buffer (40 mM Tris, 20 mM Na-acetate, 2 mM EDTA, pH 8.0). The resultant fragments, 930 bp (for B1-4) and 390 bp (for CDC) were cut from the gel. The concentration of DNA in the thus separated gel pieces was estimated to be 0.05 mg/ml. The agarose pieces cut from the gel and containing the cleaved, amplified fragments (B1-4 and CDC) were melted in a water bath at 65° C., whereafter they were allowed to cool to 37° C. 10 μl (0.5 μg) of this DNA were transferred to a semimicrotube (Sarstedt), preheated to 37° C., whereafter 1 μl of the vector pHD389 which had been cleaved with Narn and SalI were added. 1 μl 10×ligase buffer (Promega) and 1 μl T4 DNA-ligase (1 unit/μl) were also added. The ligating reaction was permitted to take place at 37° C. for 6 hours. The cleaving and ligating conditions recommended by the producer of DNA-ligase and restriction enzymes (Promega) were followed in other respects. The ligating reaction was then used to transform *E. coli*, strain LE392, which had been made competent in accordance with the rubidium-chloride/calcium-dichloride method as described by Kushner (1978). Manipulation of DNA was effected in accordance with molecular biological standard methods (Sambrook et al., 1989).

Expression System

The vector pHD389 (see FIG. 2) is a modified variant of the plasmid pHD313 (Dalböge et al., 1989). The vector which was replicated in *E. coli* (contains origin of replication from plasmid pUC19) is constructed such that DNA-fragments which have been cloned in the cleaving site for NarI will be expressed immediately after, or downstream, of the signal peptide (21 amino acids) from the envelope protein ompA from *E. coli*. Translation will be initiated from the ATG-codon which codes for the first amino acid (methionine) in the signal peptide. The construction with an *E. coli*-individual signal sequence which precedes the desired peptide enables the translated peptide to be transported to the periplasmic space in *E. coli*. This is beneficial since it reduces the risk of degradation of the desired product through the intracellular occurrent enzymes of *E. coli*. Furthermore, it is easier to purify peptides which have been exported to the periplasmatic space. Unique recognition sequences (multiple cloning sequences) for several other restriction enzymes, among them EcoRI, SalI and BamHI are present immediately downstream of the NarI cleaving site. An optimized so-called Shine-Dalgarno sequence (also called ribosomal binding site, RBS) is found seven nucleotides upstream of the ATG-codon in the signal sequence from ompA, this optimized Shbine-Dalgarno sequence binding to a complementary sequence in 16S rRNA in the ribosomes and in a manner to decide that the translation is initiated in the correct place. The transcription of such DNA as that which is co-transcribed with the signal sequence for ompA is controlled by the $P_R$-promotor from coliphage λ. The vector also contains the gene for cI857 from coliphage λ, the product of which regulates-down transcription from $P_R$ and the product of which is expressed constitutively. This cI857-mediated down-regulation of transcription from $P_R$ is heat-sensitive. Transcription which is regulated, or controlled, from this promotor will be terminated with the aid of a so-called rho-independent transcription terminating sequence which is inserted in the vector immediately downstream of the multiple cloning site. The plasmid also carries the gene for β-lactamase (from the plasmid pUC19), the product of which permits ampicillinselection of *E. coli* clones that have been transformed with the vector.

Selection of Protein LG-produced Clones

The transformed bacteria are cultivated on culture plates with LB-medium which also contained ampicillin in a concentration of 100 μg/ml. The bacteria were cultivated overnight at 30° C., whereafter they were transferred to a cultivation cabinet (42° C.) and cultured for a further four (4) hours. The plates were stored in a refrigerator overnight. On the following day, the colonies were transferred to nitrocellulose filters. The filters and culture plates were marked, so that the transferred colonies could later be identified on the culture plate. The culture plates were again incubated overnight at 30° C., so that rests of transferred bacteria colonies remaining on the plates could again grow. The plates were then stored in a refrigerator. The filter was incubated in 10% SDS for 10 minutes, so as to lyse the bacteria in the colonies on the nitrocellulose impression. Filters containing lysed bacteria were then rinsed with a blocking buffer consisting of PBS (pH 7.2) with 0.25% gelatine and 0.25% Tween-20 (four baths of 250 ml at 37° C.), whereafter the filter was incubated with radioactively (marked with $^{125}I$ according to the chloromine-T-method) marked Ig-κ-chains (20 ng/ml) in PBS with 0.1% gelatine). The incubation process took place at room temperature for four (4) hours, whereafter non-bound radioactively marked protein was rinsed-off with PBS (pH 7.2) containing 0.5M NaCl, 0.25% gelatine and 0.25% Tween-20 (four baths, 250 ml each at room temperature). All filters were exposed to X-ray film. Positive colonies on the original culture plate were identified. A number of positive colonies were recultivated on new plates and new colony-blot experiments were carried out with these plates as a starting material with the intention of identifying *E. coli* colonies which bind IgG Fc. These tests were carried out in precisely the same manner as that described above with respect to the identification of *E. coli*-colonies which expressed Ig light-chain-binding protein, with the exception that a radioactively marked($^{125}I$) IgG Fc (20 ng/ml) was used as a probe. Clones which reacted with both proteins were selected and analyzed with regard to the size of the DNA-fragment introduced in the vector. One of these clones was chosen for production of protein LG, PHDLG. The DNA taken from this clone and introduced into plasmid pHD389 was sequenced. The DNA-sequence exhibited full agreement with corresponding sequences (B1–B4 and 21 bases in B5) in the gene for protein L from *Pentostreytococcus magnus*, strain 312, and with C1DC2 sequence in group C streptococcus strain C40. The size and binding properties of the protein produced from clone PHDLG was analyzed with the aid of SDS-PAGE (see FIG. 8), dot-blot experiment (see FIG. 9) and competitive binding experiments.

Production of Protein LG

Several colonies from a culture plate with *E. coli* pHDLG were used to inoculate a preculture (LB-medium with an addition of 100 mg/l ampicillin) were cultivated at 28° C. overnight. In the morning, the preculture was transferred to a larger volume (100 times the volume of the preculture) of fresh LB-medium containing ampicillin (100 mg/l) and was cultivated in vibrating flasks (200 rpm), (or fermenters) at 28° C. When an absorbence value of 0.5 was reached at 620 nm, the cultivation temperature was raised to 40° C. (induction of transcription). The cultivation process was then continued for 4 hours (applies only to cultivation in vibrated flasks). The bacteria were centrifuged down upon termination of the cultivation process. The bacteria were then lysed at 4° C. in accordance with an osmotic shock method (Dalböge et al., 1989). The lysate was adjusted to a pH of 7. Remaining bacteria rests were centrifuged down and the supernatent then purified on IgG-sepharose, in accordance with the protocol earlier described with reference to protein G and protein L. (Sjöbring et al., 1991, Kastern et al., 1992).

The expression system gave about 30 mg/l of protein LG when cultivation in vibrated flasks. A deposition has been made at DSSM, Identification Reference DSSM E. coli LE392/pHDLG.

EXAMPLE 3

Analysis of the Binding Properties of Protein LG

Western Blot

Protein G (the C1DC2-fragment), protein L (four B-domains) and protein LG were isolated with SDS-PAGE (10% acrylamide concentration). The isolated proteins were transferred to nitrocellulose membranes in three similar copies (triplicate). Each of these membranes was incubated with radioactively marked proteins (20 ng/ml: one of the membrane-copies was incubated with human polyclonal IgG, another with human IgG Fc-fragment and the third with isolated human IgG χchains. Non-bound radioactively marked proteins were rinsed off and all filters were then exposed to X-ray film.

Slot-blot

Human polyclonal Ig-preparations and Ig-fragments were applied with the aid of a slot-blot appliances on nitrocellulose filters in given quantities (see FIG. 9) on three similar copies. Each of these membranes was incubated with radioactively marked proteins (20 ng/ml). One of the membrane copies was incubated with protein LG, another with protein L and the third with protein G. Non-bound radioactively marked proteins were rinsed-off and all filters were then exposed to X-ray film.

Figure 8:
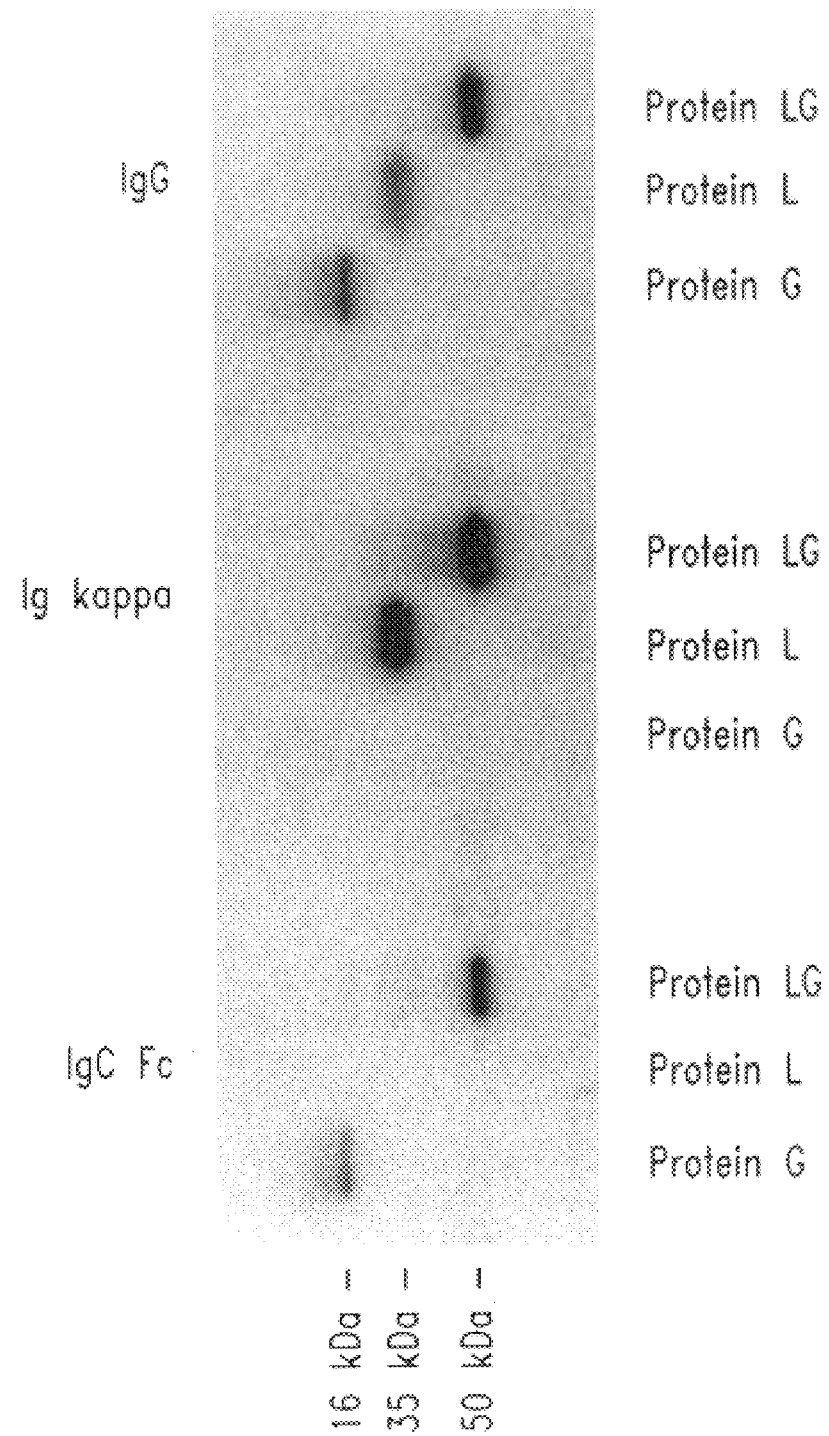
FIG. 8 illustrates Western Blot for protein G, L and LG with certain immunoglobulins and immunoglubulin fragments.
Figure 9:
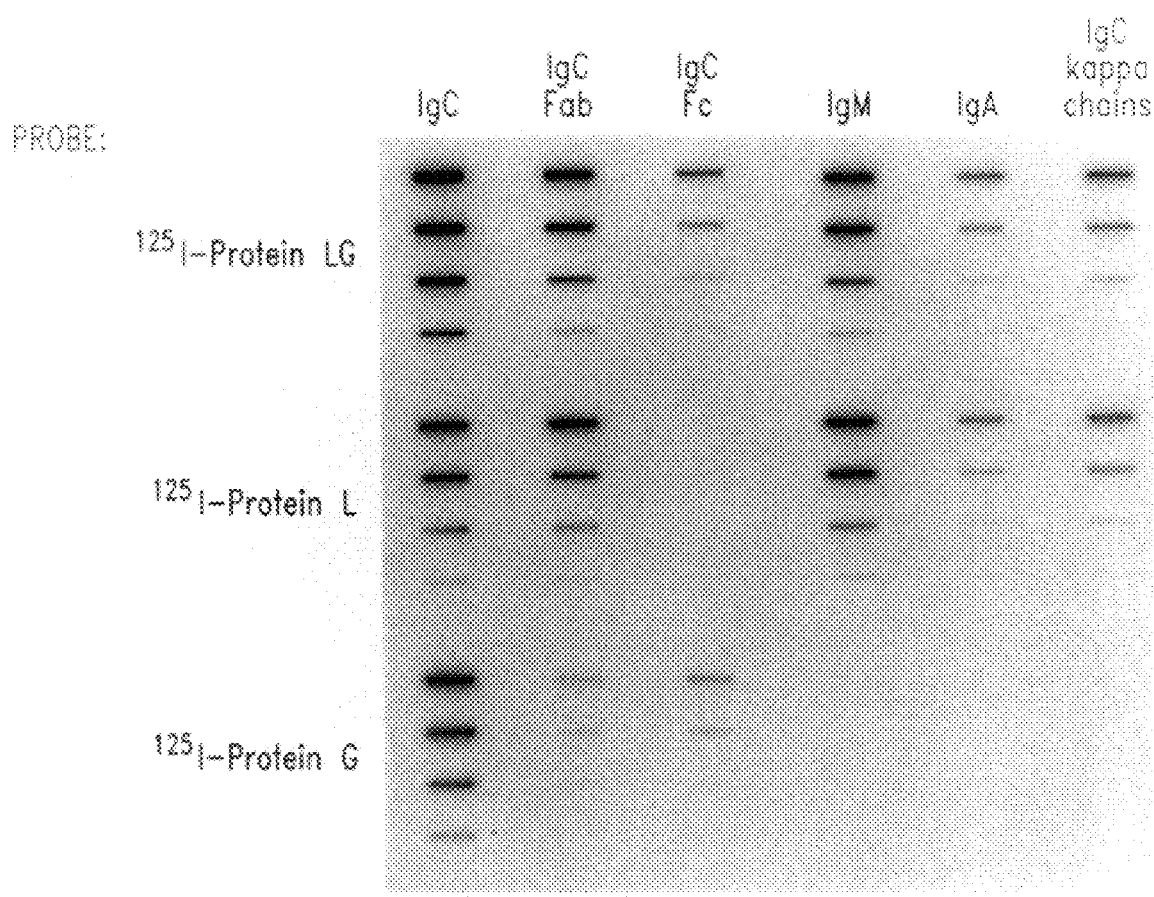
FIG. 9 illustrates Slot-Blot for protein L, G and LG with IgG, Igχ and Ig Fc.

The results are shown in FIGS. 8 and 9.

Other binding experiments have been carried out, with the following results:

TABLE

Binding of the proteins G, L and LG to immunoglobulins.

| Immunoglobulin | G | $K_a$ | L | $K_a$ | LG | $K_a$ |
|---|---|---|---|---|---|---|
| Human: | | | | | | |
| Polyclonal IgG* | + | 67 (10) | + | 9.0 | + | 20 |
| IgG subclasses | | | | | | |
| IgG$_1$ | + | 2.0 | + | | + | |
| IgG$_2$ | + | 3.1 | + | | + | |
| IgG$_3$ | + | 6.1 | + | | + | |
| IgG$_4$ | + | 4.7 | + | | + | |
| IgG fragment | | | | | | |
| Fc* | + | 6.0 (0.5) | – | | + | |
| F(ab')$_2$* | + | 0.4 (0.2) | + | | + | |
| kappa | – | | + | 1.5 | + | |
| lambda | – | | (–)[#] | | | |
| Other Ig-classes | | | | | | |
| IgM | – | | + | 11.6 | + | |
| IgA | – | | + | 10.4 | + | |
| IgE | – | | + | | + | |
| IgD | – | | | | | |
| Other Species: | | | | | | |
| Polyclonal | | | | | | |
| Monkey | + | | + | | + | |
| Rabbit | | | | | | |
| IgG | + | 70 | + | 0.074 | + | |
| IgG-Fc | + | 3.0 | – | | + | |
| IgG-F(ab')$_2$ | + | 0.44 | | | + | |
| Mouse | + | 41 | + | 2.6 | + | |
| Rat | + | 1.5 | + | 0.39 | + | |
| Goat | + | 14 | – | | + | |
| Bovine | | | | | | |
| IgG$_1$ | + | 3 | – | | + | |
| IgG$_2$ | + | 2 | – | | + | |
| Horse | + | | – | | + | |
| Guinea Pig | + | | + | | + | |
| Sheep | + | | – | | + | |
| Dog | + | | – | | + | |
| Pig | + | | + | | + | |
| Hamster | + | | | | | |
| Cat | – | | – | | | |
| Hen | – | | – | | | |
| Monclonals[&] | | | | | | |
| Mouse | | | | | | |
| IgG$_1$ | + | | + | | + | |
| IgG$_{2a}$ | + | | + | | + | |
| IgG$_{2b}$ | + | | | | + | |
| IgG$_3$ | + | | | | + | |
| IgM | – | | + | | + | |
| IgA | – | | + | | + | |
| Rat | | | | | | |
| IgG$_{2a}$ | + | | + | | + | |
| IgG$_{2b}$ | + | | | | + | |
| IgG$_{2c}$ | + | | | | + | |

$K_a$ = affinity constant ($M^{-1}$). *The numerals within parenthesis disclose the affinity of a recombinant protein G comprised of two IgG-binding domains. [#]A weak bond to lambda chains exists. [&]Binding to Pl and PLG depends on the type of light chain of Ig.

It will thus be seen that the synthesized hybrid protein LG has a broad binding activity/specificity.

We claim:

1. An isolated DNA molecule that codes for a Protein L which binds to the light chains of immunoglobulins, wherein said DNA molecule has the nucleotide sequence of Sequence ID No. 2.

2. An isolated DNA molecule that codes for a hybrid protein which binds to the light chains in immunoglobulins and to the heavy chains of immunoglobulin G, wherein said DNA molecule has the nucleotide sequence of Sequence ID No. 4.

3. An isolated DNA molecule that codes for a hybrid protein that is either:
   (a) a hybrid protein comprising (i) one or more of the B1–B5 domains of Sequence I.D. No.1, which bind to the light chains in immunoglobulins of all classes, and (ii) domains which bind to heavy chains in immunoglobulin G, or
   (b) hybrid protein (a), wherein the heavy chain-binding domains are selected from the C1 and C2 domains in protein G.

4. An isolated DNA molecule that codes for a protein having binding properties selected from the group consisting of:
   (i) the ability to bind to the light chains of immunoglobulins, and
   (ii) the ability to bind to the light chains in immunoglobulins of all classes, and the ability to bind to heavy chains in immunoglobulin G.

5. A plasmid vector, comprising a DNA molecule selected from the group consisting of:
   (a) a DNA molecule according to any one of claims 1, 2, or 3, and
   (b) a DNA molecule that codes for a protein having binding properties selected from the group consisting of (A) the ability to bind to the light chains of immunoglobulins, and (B) the ability to bind to the light chains in immunoglobulins of all classes, and the ability to bind to heavy chains in immunoglobulin G.

6. The plasmid vector of claim 5, wherein said vector is either pHDLG or pHDL.

7. A host cell, comprising the vector of claim 5.

8. The host cell of claim 7, wherein said vector is either pHDLG or pHDL.

9. The host cell of claim 7, wherein said host cell is selected from the group consisting of *E. coli*, *Bacillus subtilis*, and *Scaccharomyces cerevisiae*.

10. The host cell of claim 9, wherein said *E. coli* host cell is *E. coli* LE392.

11. The host cell of claim 10, wherein said host cell is either Identification Reference DSSM *E. coli* LE392 pHDL or Identification Reference DSSM *E. coli* LE392/pHDLG.

* * * * *